(12) United States Patent
Johal et al.

(10) Patent No.: US 6,784,341 B2
(45) Date of Patent: Aug. 31, 2004

(54) DEFENSE-RELATED SIGNALING GENES AND METHODS OF USE

(75) Inventors: Gurmukh S. Johal, Urbandale, IA (US); Dilbag Multani, Urbandale, IA (US)

(73) Assignees: Pioneer Hi-Bred International, Inc., Des Moines, IA (US); The Curators of the University of Missouri, Columbia, MO (US)

( * ) Notice: Subject to any disclaimer, the term of this patent is extended or adjusted under 35 U.S.C. 154(b) by 283 days.

(21) Appl. No.: 09/952,689

(22) Filed: Sep. 14, 2001

(65) Prior Publication Data

US 2002/0095694 A1 Jul. 18, 2002

Related U.S. Application Data

(60) Provisional application No. 60/232,538, filed on Sep. 14, 2000.

(51) Int. Cl.$^7$ .......................... A61H 1/00; C07H 21/04; C07K 14/415; C12N 5/14
(52) U.S. Cl. .......................... 800/295; 435/6; 435/69.1; 435/91.4; 435/468; 435/419; 435/252.3; 435/320.1; 530/370; 536/23.6; 800/279; 800/295
(58) Field of Search .......................... 435/6, 69.1, 468, 435/410.419, 252.3, 320.1; 530/370; 536/23.1, 23.6, 24.1, 24.3, 24.33; 800/278, 295

(56) References Cited

U.S. PATENT DOCUMENTS 4,956,282 A * 9/1990 Goodman et al. ........ 435/69.51
6,465,611 B1 * 10/2002 Xu et al. .................... 530/300

OTHER PUBLICATIONS

Database GenEmbl. Acc. No. AC105038. Birren et al. *Homo sapiens* chromosome 8, clone CTD–2351P9. Jan. 15, 2003.*
Bachem, C., et al., "Antisense Suppression of a Potato α–SNAP Homologue Leads to Alterations in Cellular Development and Assimulate Distribution,", *Plant Molecular Biology*, 2000, pp. 473–482, vol. 43, Kluwer Academic Publishers, Netherlands.

Kwong, J., et al., "Hrs Interacts with SNAP–25 and Regulates Ca$^{2+}$–Dependent Exocytosis", *Journal of Cell Science*, 2000, pp. 2273–2284, vol. 113, The Company of Biologists, Great Britain.

Okamoto, M., et al., "EHSH1/Intersectin, A Protein That Contains EH and SH3 Domains and Binds to Dynamin and SNAP–25", *The Journal of Biological Chemistry*, 1999, pp. 18446–18454, vol. 274(26), The American Society for Biochemistry and Molecular Biology, Inc. , USA.

Ungerman, C. and Wickner, W., "Vam7p, A Vacuolar SNAP–25 Homolog is Required for SNARE Complex Integrity and Vacuole Docking and Fusion", *EMBO Journal*, 1998, pp. 3269–3276, vol. 17(12), Oxford University Press, USA.

Ungerman, C., et al., " A New Role for a SNARE Protein as a Regulator of the Ypt7/Rab–Dependent Stage of Docking," *PNAS*, 2000, pp. 8889–8891, vol. 97(16).

Wei, S., et al., "Exocytotic Mechanism Studied by Truncated and Zero Layer Mutants of the C–Terminus of SNAP–25," *EMBO Journal*, 2000, pp. 1279–1289, vol. 19(6).

Weidenhaupt, M., et al., "Functional and Molecular Indentification of Novel Members of the Ubiquitous Membrane Fusion proteins α–and γ–SNAP (Soluble N–ethylmaleimide–Sensitive Factor Attachment Proteins) Families in Dictyostelium Discoideum", *Eur. J. Biochem*, 2000, pp. 2062–2070, vol. 267.

GenBank Report for Accession No. X92420, Direct Submission on Oct. 9, 1995.

GenBank Report for Accession No. AI442625, Submitted on Feb. 19, 1999.

* cited by examiner

*Primary Examiner*—Phuong T. Bui
(74) *Attorney, Agent, or Firm*—Pioneer Hi-Bred International, Inc.

(57) ABSTRACT

The invention provides isolated SNAP25 nucleic acids, their encoded proteins, and a loss-of-function phenotype of the SNAP25 gene. The present invention provides methods and compositions relating to altering SNAP25 concentration and/or composition of plants. The invention further provides recombinant expression cassettes, host cells, and transgenic plants.

14 Claims, 4 Drawing Sheets

Genomic Sequence of Rm1-B73 (WT) allele: (corrected 4-27-2000)

ccaataACTCAGGGTTAAGCAAAGCAGAACAAGAAAGCACCTCAGC
TGTCGTAGCGCTCCTCA*CCAAT*CCAATGCCGTCTTTGACCTAGCCG
GCGCCGCGTCCTTGACCGAGGAAGTAGTCGCACGCAGCACGCTC
CTATGAGCTAGTAATAATTTTCACAACCAGAATCGCGTGTCGACA
GCGCGAGCCGTAACGGAAACCGGATGGAAATG<u>GGATCC</u>AGCCGG
ACGCGGGGAGTCTGCTGTCAGGGCGCACGCCATCGAGCGACCGT
GTCCTCGCTCTTTTACCTTTCCTCCTGTCA*GGGCG*CGTGCATCCCC
TACGACCAGGGCAGCGTATATCCTTGTCGCTCTTCGTCGTCTCCCC
CCACAACTGT<u>TATA</u>TTCCCACCGGCGCCGCCGGCTCTTCGTCGTC
CTCCTCCGGGTGTGC<u>CCC</u>AGTTCGCTGCCCGTTCCCCAGCCGCCG
ATCCCTCGATCTCCGCTAGCTTCGTTCCTTCGTACAGgtgcttcacttcatcc
ttgtgctttctatctgttcttctcatattgcgtgagaattttcatttcagttcatgtgagtcgatccttcaattttaaaact
atgtatgtatgtcgggtgaacccggttcctcgattccccacaggaacggtcaggggcggacccagcaccca
ggcacctcaggcggtggcctaggctgcctcgcaggttctgattgatagaagcaagtataatatgtagaaaca
agcaagcaacgtagtatgtacacagcaaaagtataagcacaaaggatcacagtgtaatctcgcctaggctgt
ctctaaatcctgggtccgccactgggaacggttgtgtttcagttcatgggagttggtccttcattttaaaaattat
gtatgtatgccgggtgaaatgaatccggttcctcaattcaccacagGAACGGTCGAGCAGAA
ACTAGCAGCCACTCCCGAGTCCCGACTCCCGATCGCGATTACTTG
CCGCGGCACCAGTACTCCAGCGGCCACC<u>ATG</u>AGCAGCGGGAAG.
...Mu2..Insertion...CGATCCTTCTTCGCGCCCAAGAAGAAGGCCAC
CAACCCGTTCGATTCCGACTCCGACGACGACAAACCGCAGCAGC
GGCCAGCGCGGGCGTCCTCCGTGCCTCCCCCGGACGAGCAGCGG
GGCTCCTCCTCTCTTCGGCGCCGGCGACAGAGGCGGGCTCTTC
TCTTCCGCGGCCAACCATCACTACCGGAACGACTTCCGCGACGCT
GGCGGCCTTGAGGGCCAGTCCGTGCAGGAGCTGGAGGGCTACGC
GGCGTACAAGGCCGAGGAGACCACGCGCCGGACGCGGGGGTGCG
TCAGGATCGCCGAGGAGATGAGGGACACCGCATCCAAGACGCTC
GTCACCGTCCACCAGCAGGGGCAGCAGATCCACCGCACGCACAT
GATGGCCGTCGACATCGACCAGGATCTCTCCAGGgtaactatagccttttcgaattt
ctttcgtttgcggtgtggcatcagtttatgagattgtttgtaccgctagcttagttctgttcgcctgaagaggggatagtcactgttcttt
caaatctagtccgtttcagaaaccctgaaacccaacaagaggaggtgctaactgactaatttacagagggtaaattaaacctgca
atcgccaacattttgcaagttatgctgctccatttgcacaagccacaaggctaaccccgggatataaaagatcttatgctaataac
gagccttattctgctcaagtagggcataatcgcacagcactctcaatttcaaaccagaattggacagttcctgaaatcctgaaatca
gcaggtattctcgctaataactctagaaattctagtttagtggggagggattaaaacctggaagtattaacaatgacatgcttgtta
gttgttactatcggcttttgtaactgcatattgcgactatggatgctcctttgcacattgcagacatgtgacaggtgttgaataaatgttt
tggctcaatatttcagAGTGAGAAGCTATTGGGCGATCTTGGGGGTCTATTTT
CCAAAAAGTGGAAGCCAAAGAAGAATGGCGCCATCAGGGGTCCT
ATGCTAACTAGAGgtaattacttaaactggactgcatgatgaagttgatgactgaagaaacttgtactgcctggt
attggctatggtgccgtccatgactgaaaggatgcaatggtggatgcagATGATTCCTTCATAAGGAA

FIGURE 1A

GGGGAGTCATTTGGAGCAAAGGCAGAAACTAGGGCTGGCAGATC
ATCCACCTCCATCAAATGCGCGCCAATTCCGTTCTGAACCCTCAT
CAGCACTTGAGAAAGTTGAGgtactgtagacacttgtgaagctaatgcatctccagcacgt
gatgaaaaatcttgatgcgtcttgatatcctgcatctttattccataaccatctggtcgtttcttttgtagATAG
AGAAGGCAAAGCAGGATGATGATCTGTCTGATCTAAGCAACATA
CTGACGGAGCTGAAAGGGATGGCCGTTGACATGGGCTCTGAGAT
CGAGAGgtactgttacatttcgctatcttgtagactgatctgtgtggtcagtaattcatttattttcttcctgttg
tatagtcaattctcaagaaagtatccgaaacttccaaaaagaaaatactatctgtcagtttgaatgctgatagca
atctcgttagttattaaattattaatttggagtattgttgctgtgagtatgacatgtcctctgtgtttgttggattcagG
CAAACAAAAGCAATGGGGGATGCAGAGAAGGATTATGACGAGCT
GAACTTCAGGGTCAAGGGAGCAAACACTC<u>GAGCTC</u>GCCGTCTCCT
CGGGAGA<u>TAA</u>AAAAATGCATATATTCTTGTCTCTTGGATGGTCCA
TAACACATTAACTATATGGGGGCATCAAATTCTGATGATTTTGTG
CATCAGATTTTGATTAGCATTGTTACCGTGGACATGTCGGCGTGT
ATGGTAGTTGAGACATATTTTATATGTTTGCTTCTTTTTTCTATTTT
TTTAGCATTGCACGAGCTTAGGATTTCAGTGGATTTTACATGGAA
AACCTTGTCTGAT<u>TAG</u>AAA

FIGURE 1B

DEFENSE-RELATED SIGNALING GENES AND METHODS OF USE

CROSS-REFERENCE TO RELATED APPLICATIONS

This application claims the benefit of U.S. Provisional Application No. 60/232,538 filed on Sep. 14, 2000, the contents of which are herein incorporated by reference.

TECHNICAL FIELD

The present invention relates to plant molecular biology and the genetic manipulation of plants, particularly to novel defense-related signaling genes and proteins and their uses in regulating cell death and disease resistance in plants.

BACKGROUND OF THE INVENTION

A host of cellular processes enable plants to defend themselves from disease caused by pathogenic agents. These processes apparently form an integrated set of resistance mechanisms that is activated by initial infection and serves to limit further spread of the invading pathogenic microorganism.

Generally, after a plant recognizes a potentially pathogenic microbe the plant responds by inducing several local responses in the cells immediately surrounding the infection site. Genetic factors in both the host and the pathogen determine the specificity of these local responses, which can be very effective in limiting the spread of infection. The most commonly observed resistance response is termed the "hypersensitive response" (HR). In the hypersensitive response, cells contacted by the pathogen (and often neighboring cells) rapidly collapse and dry in a necrotic fleck. Other responses include the deposition of callose, the physical thickening of cell walls by lignification, and the synthesis of various small molecules and proteins with antibiotic properties. Components of many of these responses are deployed outside the plasma membrane and therefore need to be secreted.

Necrosis in plants also results from other causes. Many environmental and genetic factors can cause general leaf necrosis in maize and other plants. In addition, numerous recessive and dominant mutants have been reported which cause discrete necrotic lesions to form. These "lesion mutants" produce a phenotype that mimics disease lesions caused by various pathogenic organisms, even in the absence of any invading pathogens. Thus, lesion mutants are also called "lesion mimics," "disease mimics," or "disease lesion mimics."

Lesion mimic mutations of maize have been shown to be specified by more than forty independent loci. For example, lesi, a temperature-sensitive conditional lethal mutant in maize, mimics the appearance of *Helminthosporium maydis* lesions on susceptible maize. It is intriguing that more than two thirds of lesion mimic mutations display a partially dominant, gain-of-function inheritance, making this the largest class of dominant mutants in maize and suggesting the involvement of a signaling pathway in the induction of lesions in these mutations. Similar mutations have also been discovered in other plants, including Arabidopsis, barley and rice.

The pattern of lesion spread on leaves is a function of two factors: lesion initiation and individual lesion enlargement. For example, the lethal leaf spot-1(lls1) mutation of maize, which is inherited in a recessive monogenic fashion, is characterized by the formation of scattered, necrotic leaf spots (lesions) that expand continuously to engulf the entire tissue. Spots caused by lls1 show a striking resemblance to lesions incited by race 1 of *Cochliobolus* (*Helminthosporium*) *carbonum* on susceptible maize.

Despite availability of a large number of lesion mimic mutations in plants, the mechanistic basis and significance of this phenomenon have remained largely elusive. Similarly, an understanding of the molecular and cellular events that are responsible for plant disease resistance remains rudimentary. This is especially true of the events controlling the earliest steps of active plant defense, which include recognition of a potential pathogen and transfer of the cognitive signal throughout the cell and surrounding tissue.

Exocytosis is the final event in the secretory pathway. It requires the fusion of the secretory vesicle membrane with the plasma membrane and results in the release of vesicle contents from the cell interior to the outside. Targeting and fusion of transport vesicles requires many membrane bound and cytosolic factors, and much attention has been paid to SNAREs. The term SNARE is used to designate two distinct families of membrane anchored proteins that share structural motifs. While v-SNAREs are present on vesicle membranes, t-SNAREs are found mainly on the target membrane, plasma membrane for example. Both t- and v-SNAREs are anchored into their respective membranes by either a c-terminal hydrophobic domain or by post-translational attachment of lipids. Interaction of particular t- and v-SNAREs provides the specificity that is a hallmark of vesicle targeting (recognition) and fusion during exocytosis.

Most of the information on SNAP-25 function comes from studies of synapses in nerve terminals. Briefly, SNAP-25 is localized to the cytoplasmic side of presynaptic membranes. There it forms a ternary complex with syntaxin-1, another t-SNARE like itself, and VAMP-2 (also called synaptobrevin), the synaptic vesicle associated v-SNARE. A hexameric cytosolic ATPase [from the family of AAA-type ATPases, and also known as NSF (N-ethylmaleimide sensitive factor)], dissociates this complex during priming of the exocytotic complex with the assistance of another protein, SNAP (soluble NSF attachment protein). Subsequent reassembly is promoted by SNAP-25 and may drive calcium-triggered vesicle membrane fusion. See, for example, Kwong, et al. (2000) *Journal of Cell Science* 113:2273–2284.

In addition to phytoalexins, a number of other compounds, both proteinaceous and non-proteinaceous, are secreted in the extracellular environment in the vicinity of attempted infection. These include a number of PR proteins, precursors of callose, suberin and lignification, and a variety of phenylpropanoids and their derivatives. Impairment in the secretion of these compounds is likely to weaken plant's resistance to pathogens. Conversely, accelerated or enhanced secretion of these molecules may lead to a more vigorous and effective resistance response. Thus, there is an art recognized need for compositions and methods that modulate the exocytosis of defense proteins or metabolites that protect plants against pathogen attack and disease.

Clearly, exocytosis is an essential cellular process with roles in many physiological functions. In addition, defective exocytosis has been implicated in diverse human diseases, including polycistic kidney disease, creutzfeld-jakob disease, cancer, tetanus and botulism. Thus compositions and methods of modulating exocytosis may contribute methods of modulating human diseases and physiology.

SUMMARY OF THE INVENTION

Generally, it is the object of the present invention to provide nucleic acids and proteins relating to plant defense-related signaling, for example, nucleic acids having a nucleotide sequence as set forth in SEQ ID NO:1, 2, 4, or 6, and polypeptides having an amino acid sequence as set forth in SEQ ID NO:3, 5, or 7. It is an object of the present invention to provide transgenic plants comprising the nucleic acids of the present invention. It is another object of the present invention to provide methods for modulating, in a transgenic plant, the expression of the nucleic acids of the present invention.

Therefore, in one aspect, the present invention relates to an isolated nucleic acid comprising a member selected from the group consisting of (a) a polynucleotide encoding a polypeptide of the present invention; (b) a polynucleotide amplified from a Zea mays nucleic acid library using the primers of the present invention; (c) a polynucleotide comprising at least 20 contiguous bases of the polynucleotides of the present invention; (d) a polynucleotide encoding a plant SNAP25 protein; (e) a polynucleotide having at least 50% sequence identity to the polynucleotides of the present invention; (f) a polynucleotide comprising at least 25 nucleotide in length which hybridizes under low stringency conditions to the polynucleotides of the present invention; and (g) a polynucleotide complementary to a polynucleotide of (a) through (f). The isolated nucleic acid can be DNA, RNA, or a synthetic analog thereof.

In another aspect, the present invention relates to vectors comprising the polynucleotides of the present invention. Also the present invention relates to recombinant expression cassettes comprising a nucleic acid of the present invention operably linked to a promoter.

In another aspect, the present invention is directed to a host cell into which has been introduced the recombinant expression cassette. In yet another aspect, the present invention relates to a transgenic plant or plant cell comprising a recombinant expression cassette with a promoter operably linked to any of the isolated nucleic acids of the present invention. For example, plants containing the recombinant expression cassette of the present invention could include but are not limited to maize, soybean, sunflower, sorghum, canola, wheat, alfalfa, cotton, rice barley, and millet. The present invention also provides transgenic seed from the transgenic plant.

In another aspect, the present invention relates to an isolated protein selected from the group consisting of (a) a polypeptide comprising at least 25 contiguous amino acids of SEQ ID NO:3, 5, or 7; (b) a polypeptide which is a plant SNAP25; (c) a polypeptide comprising at least 55% sequence identity to SEQ ID NO:3, 5, or 7; (d) a polypeptide encoded by a nucleic acid of the present invention; (e) a polypeptide characterized by SEQ ID NO:3, 5, or 7; and (f) a conservatively modified variant of SEQ ID NO:3, 5, or 7.

Methods of modulating the level of protein in a plant are also provided. These methods comprise introducing into a plant cell a recombinant expression cassette comprising a polynucleotide of the present invention operably linked to a promoter; culturing the plant cell under appropriate growing conditions to produce a regenerated plant; and inducing expression of the polynucleotide for a time sufficient to modulate the protein of the present invention in the plant. For example, protein levels could be modulated in plants such as maize, soybean, sunflower, sorghum, canola, wheat, alfalfa, cotton, rice, barley, and millet. The level of protein in the plant can either be increased or decreased.

The compositions of the invention include isolated nucleic acid molecules and proteins. The nucleic acid molecules of the invention are polynucleotides having the sequences set forth in SEQ ID NO:1, 2, 4, or 6, and fragments thereof. The maize Rm1 nucleotide sequence is set forth in SEQ ID NO:1. The maize SNAP25 nucleotide sequence is set forth in SEQ ID NO:2, and the maize SNAP25 amino acid sequence is set forth in SEQ ID NO:3. The rice SNAP25 nucleotide sequence is set forth in SEQ ID NO:4, and the rice SNAP25 amino acid sequence is set forth in SEQ ID NO:5. The wheat SNAP25 sequence is set forth in SEQ ID NO:6, and the wheat SNAP25 amino acid sequence is set forth in SEQ ID NO:7. The compositions of the invention also comprise fragments and variants of the disclosed sequences. A nucleotide sequence of the invention may be 26 contiguous nucleotides of a disclosed sequence, or a nucleotide sequence of the invention will have at least 75% sequence identity to a disclosed nucleotide sequence and encode a polypeptide having defense-related activity.

The nucleotide sequences of the invention may be presented in vectors or expression cassettes. In an expression cassette, the nucleotide sequence of the invention is operably linked to a heterologous promoter that drives expression in the host cell. The host cell may be a plant cell, microorganism, or animal cell.

The invention also comprises plants and plant cells containing the isolated nucleic acid molecules of the invention. An embodiment of the invention is a plant having stably incorporated into its genome at least one polynucleotide operably linked to a heterologous promoter active in the plant.

BRIEF DESCRIPTION OF THE DRAWINGS

FIGS. 1A and 1B show the genomic sequence of the wild-type allele of Rm1 set forth in SEQ ID NO:1. The ATG start codon is located at nucleotides 1014–1016 of this sequence. The Mu2 element (not part of this sequence) that caused the original rm1 mutation was inserted at nucleotide 1029 in exon 1 of the gene, as shown in FIG. 1.

DETAILED DESCRIPTION OF THE INVENTION

Overview

Figure 2:
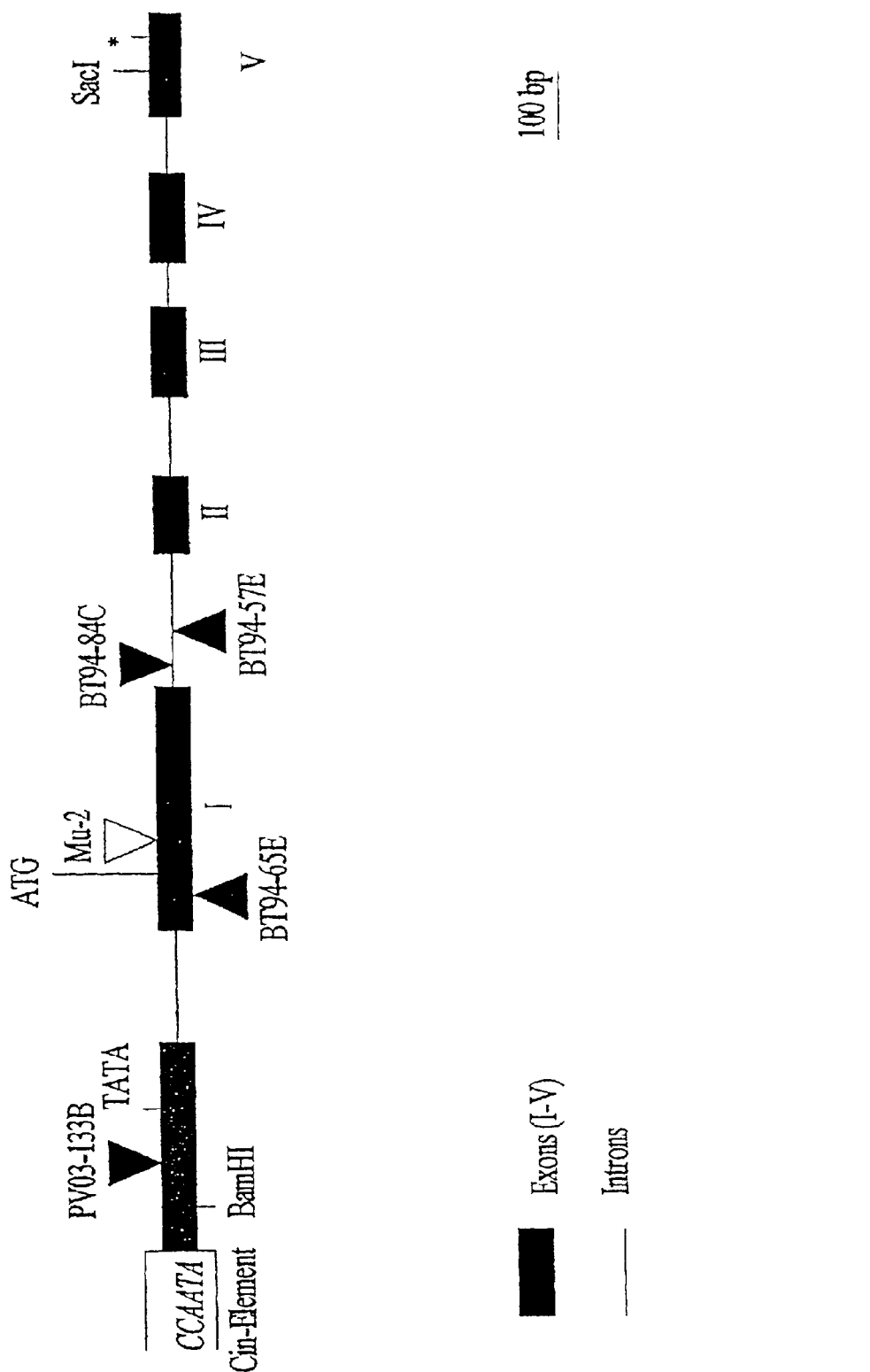
FIG. 2 shows a diagrammatic representation of the structure of the Rm1 gene, which has 5 exons (shown as solid rectangles) and 5 introns (indicated by thin lines). The sizes of exons 1, 2, 3, 4 and 5 are 435 bp (from nucleotides 1014–1448), 94 bp (2018–2111 nts), 128 bp (2223–2350 nts), 98 bp (2463–2560 nts), and 97 bp (2785–2881 nts) respectively. Intron 1 (436 bp) is in the 5' untranslated region of Rm1 (489–924 nts). Introns 2, 3, 4 and 5 are 569 bp (1449–2017 nts), 111 bp (2112–2222 nts), 112 bp (2351–2462 nts), and 224 bp (2561–2784 nts), respectively. The position of the Mu2 insertion in the original rm1 mutant allele is indicated by an open triangle. The positions of Mu insertions in the rm1 alleles derived from TUSC analysis are indicated by solid triangles. A Cin transposable element [(Shepherd et al., Nature 307:185–188 (1984)] is shown located 5' of the Rm1 gene.

The present invention springs from the creation of a maize gene mutation which causes necrotic lesions. This mutation has been designated "rust mimic-1" because the lesions are similar in appearance to fungal rust diseases of maize. Rust mimic 1 (rm1) is a recessive single-gene mutation that was discovered in a maize population active in mutator activity, a transposable element system in maize. The gene responsible for the rust mimic phenotype and its wild-type counterpart were identified and cloned from this population, providing the nucleotide and amino acid sequences of the present invention.

The amino acid residues of the present invention exhibit a high degree of sequence and structural homology with SNAP-25, a synaptosome associated protein of 25 kDa. Although it was initially identified because of its involvement in neurotransmitters release, it is now well established that SNAP-25 belongs to a family of evolutionary conserved plasma membrane proteins whose members act as SNAP receptors (SNAREs) during several types of exocytotic processes.

The molecular machinery mediating exocytosis is largely conserved from yeast to humans. RMI shares structural homology with SNAP-25, a key component of the molecular machinery of exocytosis. Thus, in an embodiment the polypeptides of the invention function in exocytosis. The polypeptides of the invention may participate in the exocytosis of any plant metabolite, including but not limited to, primary metabolites, such as the precursors of cell wall biosynthesis, or cytokinesis, or, preferably, secondary metabolites. Exactly what may be blocked has not been looked into yet, but the normal growth and development of the rm1 mutant argues that it may not be the secretion of the building blocks of plant cells such as the precursors of cell wall biosynthesis or cytokinesis. It could be a secondary metabolite, however, as plants are known to accumulate vast amounts of such compounds in response to developmental and environmental signals. Moreover, some of these metabolites, especially those involved in the defense response (phytoalexins, for example), are also phytotoxic if they accumulate beyond a certain threshold. It is interesting to note in this connection that another mutant, in which resistance to a non-pathogenic form of *Cochliobolos carbonum* seems to be compromised, segregates along with the rm1 phenotype. However, it remains to be established that whether the two phenotypes are manifestations of the same molecular defect or are the results of separate but tightly linked mutations.

Accordingly, another embodiment of the invention features isolated proteins and polypeptides of SEQ ID NOS:3, 5 or 7 having a "defense-related activity". Such defense-related activity includes for example, modulating a plant defense response; modulating disease resistance; modulating vesicle transport, modulating exocytosis; modulating membrane fusion; and the like.

The present invention provides, among other things, compositions and methods for modulating (i.e., increasing or decreasing) the level of polynucleotides and polypeptides of the present invention in plants. In particular, the polynucleotides and polypeptides of the present invention can be expressed temporally or spatially, e.g., at developmental stages, in tissues, and/or in quantities which are uncharacteristic of non-recombinantly engineered plants. Thus, the present invention provides utility in such exemplary applications as enhanced disease resistance in plants.

The present invention also provides isolated nucleic acid comprising polynucleotides of sufficient length and complementarity to a gene of the present invention to use as probes or amplification primers in the detection, quantitation, or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions, or additions), for monitoring upregulation of expression or changes in enzyme activity in screening assays of compounds, for detection of any number of allelic variants (polymorphisms), orthologs, or paralogs of the gene, or for site-directed mutagenesis in eukaryotic cells (see, e.g., U.S. Pat. No. 5,565,350). The isolated nucleic acids of the present invention can also be used for recombinant expression of their encoded polypeptides, or for use as immunogens in the preparation and/or screening of antibodies. The isolated nucleic acids of the present invention can also be employed for use in sense or antisense suppression of one or more genes of the present invention in a host cell, tissue, or plant. Attachment of chemical agents, which bind, intercalate, cleave and/or crosslink to the isolated nucleic acids of the present invention can also be used to modulate transcription or translation. The present invention also provides isolated proteins comprising a polypeptide of the present invention (e.g., preproenzyme, proenzyme, or enzymes).

The invention is drawn to compositions and methods for inducing resistance in a plant to plant pests. Accordingly, the compositions and methods are also useful in protecting plants against fungal pathogens, viruses, nematodes, insects and the like.

By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen is minimized or lessened.

By "antipathogenic compositions" is intended that the compositions of the invention have antipathogenic activity and thus are capable of suppressing, controlling, and/or killing the invading pathogenic organism. An antipathogenic composition of the invention will reduce the disease symptoms resulting from pathogen challenge by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens.

Assays that measure antipathogenic activity are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. For example, a plant either expressing an antipathogenic polypeptide or having an antipathogenic composition applied to its surface shows a decrease in tissue necrosis (i.e., lesion diameter) or a decrease in plant death following pathogen challenge when compared to a control plant that was not exposed to the antipathogenic composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107–15111, herein incorporated by reference.

Furthermore, in vitro antipathogenic assays include, for example, the addition of varying concentrations of the antipathogenic composition to paper disks and placing the disks on agar containing a suspension of the pathogen of interest. Following incubation, clear inhibition zones develop around the discs that contain an effective concentration of the antipathogenic polypeptide (Liu et al. (1994) *Plant Biology* 91:1888–1892, herein incorporated by reference). Additionally, microspectrophotometrical analysis can be used to measure the in vitro antipathogenic properties of a composition (Hu et al. (1997) *Plant Mol. Biol.* 34:949–959 and Cammue et al. (1992) J. Biol. Chem. 267: 2228–2233, both of which are herein incorporated by reference).

Pathogens of the invention include, but are not limited to, viruses or viroids, bacteria, insects, fungi, and the like. Viruses include tobacco or cucumber mosaic virus, ringspot virus, necrosis virus, maize dwarf mosaic virus, etc. Specific fungal and viral pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae (Phomopsis sojae), Diaporthe phaseolorum* var. *caulivora, Sclerotium rolfsii, Cercospora kikuchii, Cercospora sojina, Peronospora manshurica, Colletotrichum dematium (Colletotichum truncatum), Corynespora cassuicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata,* Soybean mosaic virus, *Glomerella glycines,* Tobacco Ring spot virus, Tobacco Streak virus, *Phakopsora pachyrhizi, Pythium aphanidermatum, Pythium ultimum, Pythium debaryanum,* Tomato spotted wilt virus, *Heterodera glycines Fusarium solani;* Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata;* Alfalfa: *Clavibater michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusar-atrum, Xanthomonas campestris* p.v. *alfalfae, Aphanomyces euteiches, Stemphylium herbarum, Stemphylium alfalfiae;* Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora triticirepentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum,* High Plains Virus, European wheat striate virus; Sunflower: *Plasmophora halstedii, Sclerotinia sclerotiorum,* Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* p.v. *Carotovora, Cephalosporium acremonium, Phytophthora cryptogea, Albugo tragopogonis;* Maize: *Fusarium moniliforme* var. *subglutinans, Erwinia stewartii, Fusarium moniliforme, Gibberella zeae (Fusarium graminearum), Stenocarpella maydi (Diplodia maydis), Pythium irregulare, Pythium debaryanum, Pythium graminicola, Pythium splendens, Pythium ultimum, Pythium aphanidermatum, Aspergillus flavus, Bipolaris maydis* O,T *(Cochliobolus heterostrophus), Helminthosporium carbonum* I, II & III *(Cochliobolus carbonum), Exserohilum turcicum* I, II & III, *Helminthosporium pedicellatum, Physoderma maydis, Phyllosticta maydis, Kabatie-maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganese* subsp. *nebraskense, Trichoderma viride,* Maize Dwarf Mosaic Virus A & B, Wheat Streak Mosaic Virus, Maize Chlorotic Dwarf Virus, *Claviceps sorghi, Pseudonomas avenae, Erwinia chrysanthemi* p.v. *Zea, Erwinia corotovora, Cornstunt spiroplasma, Diplodia macrospora, Sclerophthora macrospora, Peronosclerospora sorghi, Peronosclerospora philippinesis, Peronosclerospora maydis, Peronosclerospora sacchari, Spacelotheca reiliana, Physopella zea, Cephalosporium maydis, Caphalosporium acremonium,* Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola (Glomerella graminicola), Cercospora sorghi, Gloeocercospora sorghi, Ascochyta sorghina, Pseudomonas syringae* p.v. *syringae, Xanthomonas campestris* p.v. *holcicola Pseudomonas andropogonis, Puccinia purpurea, Macrophomina phaseolina, Perconia circinata, Fusarium moniliforme, Alternaria alternate, Bipolaris sorghicola, Helminthosporium sorghicola, Curvularia lunata, Phoma insidiosa, Pseudomonas avenae (Pseudomonas alboprecipitans), Ramulispora sorghi, Ramulispora sorghicola, Phyllachara sacchari, Sporisorium reilianum (Sphacelotheca reiliana), Sphacelotheca cruenta, Sporisorium sorghi,* Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola,* etc.

The isolated nucleic acids and proteins of the present invention can be used over a broad range of plant types, particularly monocots such as the species of the family Gramineae including Sorghum (e.g., *S. bicolor*), Oryza, Avena, Hordeum, Secale, Triticum and Zea, and dicots such as Glycine. The isolated nucleic acid and proteins of the present invention can also be used in species from the genera: Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Pisum, Phaseolus, Lolium, and Allium.

The present invention may be used for transformation of any plant species, including, but not limited to, monocots and dicots. Examples of plant species of interest include, but are not limited to, corn (*Zea mays*), Brassica sp. (e.g., *B. napus, B. rapa, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (Lathyrus spp.), and members of the genus Cucumis such as cucumber (*C. sativus*), cantaloupe (*C. cantalupensis*), and musk melon (*C. melo*). Ornamentals include azalea (Rhododendron spp.), hydrangea (*Macrophylla hydrangea*), hibiscus (*Hibiscus rosasanensis*), roses (Rosa spp.), tulips (Tulipa spp.), daffodils (Narcissus spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, Brassica, soybean, cotton, safflower, peanut, sorghum, wheat, millet, tobacco, etc.), more preferably corn and soybean plants, yet more preferably corn plants.

Additional plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Definitions

Units, prefixes, and symbols may be denoted in their SI accepted form. Unless otherwise indicated, nucleic acids are written left to right in 5' to 3' orientation, amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, Persing, ed., American Society for Microbiology, Washington, D.C. (1993). The product of amplification is termed an amplicon.

As used herein, "antisense orientation" includes reference to a polynucleotide sequence which is operably linked to a promoter in an orientation where the anti-sense strand is transcribed. It is recognized that with these nucleotide sequences, anti-sense constructions, complementary to at least a portion of the messenger RNA (mRNA) for the sequences of the invention can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate Macronucleus, may be used when the nucleic acid is expressed therein.

When the nucleic acid is prepared or altered synthetically, advantage can be taken of known codon preferences of the intended host where the nucleic acid is to be expressed. The nucleotide sequences of interest may be optimized for increased expression in the transformed plant. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al., *Nucl. Acids Res.* 17:477–498 (1989)). Where appropriate, the gene(s) may be optimized for increased expression in the transformed plant. That is, the genes can be synthesized using plant-preferred codons for improved expression. See, for example, Campbell and Gowri (1990) *Plant Physiol.* 92: 1–11 for a discussion of host-preferred codon usage. Methods are available in the art for synthesizing plant-preferred genes. Thus, the maize preferred codon for a particular amino acid might be derived from known maize gene sequences. Maize codon usage for 28 genes from maize plants is listed in Table 4 of Murray et al., cited supra. See, for example, U.S. Pat. Nos. 5,380,831, 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. Constructs containing the native promoter sequences may be used. Such constructs would change expression levels of the defense related polypeptide in the host cell. Thus, the phenotype of the host cell (i.e., plant or plant cell) is altered. A heterologous protein may originate from a foreign species, or, if from the same species, is substantially modified from its original form by deliberate human intervention.

By "host cell" is meant a cell which contains a vector and supports the replication and/or expression of the vector. Host cells may be prokaryotic cells such as *E. coli*, or eukaryotic cells such as yeast, insect, amphibian, or mammalian cells. Host cells may be monocotyledonous or dicotyledonous plant cells. For example, a monocotyledonous host cell may be a maize host cell.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The invention encompasses isolated or substantially purified nucleic acid or protein compositions. An "isolated" or "purified" nucleic acid molecule or protein, or biologically active portion thereof, is substantially or essentially free from components that normally accompany or interact with the nucleic acid molecule or protein as found in its naturally occurring environment. Thus, an isolated or purified nucleic acid molecule or protein is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, preferably culture medium represents less than about 30%, 20%, 10%, 5%, or 1% (by dry weight) of chemical precursors or non-protein-of-interest chemicals.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes of that pair to be followed. Use of one or a plurality of markers may define a genotype.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual*, $2^{nd}$ ed., Vol. 1–3 (1989); and *Current Protocols in Molecular Biology*, Ausubel et al., eds., Current Protocols, Greene Publishing Associates, Inc. and John Wiley & Sons, Inc. (1994).

As used herein, "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. "Plant cell" as used herein includes, without limitation, seeds, suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to transformation techniques, including both monocotyledonous and dicotyledonous plants. For example, plants which can be used in the methods of the invention include but are not limited to maize, soybean, sunflower, sorghum, canola, wheat, alfalfa, cotton, rice, barley, and millet.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide (s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases (for example, inosine) or modified bases (for example, tritylated bases) are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide," "peptide," and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide," "peptide," and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not always entirely linear. For instance, polypeptides may be branched as a result of ubiquitination, and they may be circular, with or without branching, generally as a result of post-translation events, including natural processing events and events brought about by human manipulation which do not occur naturally. Circular, branched and branched circular polypeptides may be synthesized by natural non-translation processes and by entirely synthetic methods, as well. Further, this invention contemplates the use of both the methionine containing and the methionine-less amino terminal variants of the protein of the invention.

By "domain" is intended a sequence motif (i.e., a subsequence of a larger sequence) that confers certain properties on a sequence containing it. Such a sequence motif may be either a nucleotide or amino acid sequence and be contained within either a polynucleotide or a polypeptide, respectively. A domain of a polypeptide may confer an improved property of interest, such as a broader spectrum of pathogen resistance. Likewise, a domain may have a regulatory function. For example, a specific cis-acting sequence motif within the promoter sequences of the invention may confer improved regulatory functions, such as increased pathogen inducibility. Domains typically perform their functions whether they are found in their native polynucleotide or polypeptide sequence or if they are isolated and placed within another polynucleotide sequence. Thus, a protein domain conferring pathogen resistance may be expressed in isolation, apart from its native polypeptide setting, or it may be placed into an unrelated polypeptide to create a novel polypeptide and there confer the attribute of pathogen resistance on a cell expressing the novel polypeptide.

As used herein, "promoter" includes reference to a region of DNA upstream from the start of transcription and involved in recognition and binding of RNA polymerase and other proteins to initiate transcription. The transcriptional initiation region, the promoter, may be native or analagous or foreign or heterologous to the host cell. A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such as Agrobacterium or Rhizobium. Examples of promoters under developmental control include promoters that preferentially initiate transcription in certain tissues, such as leaves, roots, or seeds. Such promoters are referred to as "tissue-preferred." Promoters who initiate transcription only in certain tissue are referred to as "tissue-specific." A "cell-type-preferred" promoter primarily drives expression in certain cell types in one or more organs, for example, vascular cells in roots or leaves. An "inducible" or "repressible" promoter is a promoter which is under environmental control. Examples of environmental conditions that may affect transcription by inducible promoters include anaerobic conditions or the presence of light. Tissue specific, tissue preferred, cell type preferred, and inducible promoters constitute the class of "non-constitutive" promoters. A "constitutive" promoter is a promoter which is active under most environmental conditions.

As used herein, "recombinant" includes reference to a cell or vector that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct generated recombinantly or synthetically with a series of specified nucleic acid elements, which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter. Expression cassettes for expression in a host cell of interest are described in more detail elsewhere herein.

The term "residue" or "amino acid residue" or "amino acid" are used interchangeably herein to refer to an amino acid that is incorporated into a protein, polypeptide, or peptide (collectively, "protein"). The amino acid may be a naturally occurring amino acid and, unless otherwise limited, may encompass non-natural analogs of natural amino acids that can function in a similar manner as naturally occurring amino acids.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire sequences set forth herein in SEQ ID NO: 1, 2, 3, 4, 5, 6 or 7 or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species. Thus, isolated sequences that encode for a protein of the invention and which hybridize under stringent conditions to the sequences disclosed herein in SEQ ID NO:1, 2, 4, or 6, or to fragments thereof, are encompassed by the present invention.

In a PCR approach, oligonucleotide primers can be designed for use in PCR reactions to amplify corresponding DNA sequences from cDNA or genomic DNA extracted from any plant or other organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the nucleic acid sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire sequence disclosed herein in SEQ ID NO: 1, 2, 4, 6, or one or more portions thereof, may be used as a probe capable of specifically hybridizing to corresponding sequences and messenger RNAs. To achieve specific hybridization under a variety of conditions, such probes include sequences that are unique among defense-related sequences of the invention and are preferably at least about 10 nucleotides in length, and most preferably at least about 20 nucleotides in length. Such probes may be used to amplify corresponding defense-related sequences from a chosen plant or organisms by PCR. This technique may be used to isolate additional coding sequences from a desired plant or other organism or as a diagnostic assay to determine the presence of coding sequences in a plant or other organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA—DNA hybrids, the $T_m$ can be approximated from the equation of Meinkoth and Wahl (1984) *Anal. Biochem.* 138:267–284: $T_m$=81.5° C.+16.6(log M)+0.41(% GC)−0.61 (% form)− 500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

As used herein, "transgenic plant" or "transformed plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" or "transformed" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" or "transformed" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons and thus can replicate extra-genomically. Expression vectors permit transcription of a nucleic acid inserted therein.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad. Sci.* 85:2444–2448; the algorithm of Karlin and Altschul (1990) *Proc. Natl. Acad. Sci. USA* 872264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis. USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al. (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.nlm.nih.gov. Alignment may also be performed manually by inspection.

Unless otherwise stated, sequence identity/similarity values provided herein refer to the value obtained using GAP version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48: 443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

Nucleic Acids

The present invention provides, among other things, isolated nucleic acids of RNA, DNA, and analogs and/or chimeras thereof, comprising a polynucleotide of the present invention. In one embodiment, the nucleic acids provided comprise the *Zea mays* SNAP25 genomic sequence set forth in SEQ ID NO:1 and shown in FIG. 1; the *Zea mays* SNAP25 cDNA sequence set forth in SEQ ID NO:2; the *Oryza sativa* SNAP25 cDNA sequence set forth in SEQ ID NO:4; and the *Triticum aestivum* SNAP25 cDNA sequence set forth in SEQ ID NO:6.

A polynucleotide of the present invention is inclusive of:
- (a) a polynucleotide encoding a polypeptide of SEQ ID NO:3, 5, or 7, including exemplary polynucleotides of SEQ ID NO:1, 2, 4, or 6;
- (b) a polynucleotide which is the product of amplification from a *Zea mays* nucleic acid library using primer pairs which selectively hybridize under stringent conditions to loci within a polynucleotide selected from the group consisting of SEQ ID NO:1 or 2;
- (c) a polynucleotide which selectively hybridizes to a polynucleotide of (a) or (b);
- (d) a polynucleotide having a specified sequence identity with polynucleotides of (a), (b), or (c);
- (e) complementary sequences of polynucleotides of (a), (b), (c), or (d);
- (f) a polynucleotide comprising at least a specific number of contiguous nucleotides from a polynucleotide of (a), (b), (c), (d), or (e); and
- (g) an isolated polynucleotide made by the process of: 1) providing a full-length enriched nucleic acid library, 2) selectively hybridizing the polynucleotide to a polynucleotide of (a), (b), (c), (d), (e), or (f), thereby isolating the polynucleotide from the nucleic acid library.

The present invention provides, among other things, isolated nucleic acids of RNA, DNA, and analogs and/or chimeras thereof, comprising a polynucleotide of the present invention.

A. Polynucleotides Encoding a Polypeptide of the Present Invention

The present invention provides isolated nucleic acids comprising a polynucleotide of the present invention, wherein the polynucleotide encodes a polypeptide of the present invention. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule (so-called "silent variations"). Thus, each silent variation of a nucleic acid, which encodes a polypeptide of the present invention, is implicit in each described polypeptide sequence and is within the scope of the present invention. Accordingly, the present invention includes polynucleotides of the present invention and polynucleotides encoding a polypeptide of the present invention.

B. Polynucleotides Amplified from a Plant Nucleic Acid Library

The present invention provides an isolated nucleic acid comprising a polynucleotide of the present invention, wherein the polynucleotides are amplified, under nucleic acid amplification conditions, from a plant nucleic acid library. Nucleic acid amplification conditions for each of the variety of amplification methods are well known to those of ordinary skill in the art. The plant nucleic acid library can be constructed from a monocot such as a cereal crop. Exemplary cereals include corn, sorghum, alfalfa, canola, wheat, or rice. The plant nucleic acid library can also be constructed from a dicot such as soybean. *Zea mays* lines B73, PHRE1, A632, BMS-P2#10, W23, and Mo17 are known and publicly available. Other publicly known and available maize lines can be obtained from the Maize Genetics Cooperation (Urbana, Ill.). Wheat lines are available from the Wheat Genetics Resource Center (Manhattan, Kans.).

The nucleic acid library may be a cDNA library, a genomic library, or a library generally constructed from nuclear transcripts at any stage of intron processing. cDNA libraries can be normalized to increase the representation of relatively rare cDNAs. In optional embodiments, the cDNA library is constructed using an enriched full-length cDNA synthesis method. Examples of such methods include Oligo-Capping (Maruyama and Sugano, *Gene* 138:171–174 (1994)), Biotinylated CAP Trapper (Carninci, et al. *Genomics* 37:327–336 (1996)), and CAP Retention Procedure (Edery et al., *Molecular and Cellular Biology* 15:3363–3371 (1995)). Rapidly growing tissues or rapidly dividing cells may be used as an mRNA source for construction of a cDNA library. Growth stages of corn is described in "How a Corn Plant Develops," Special Report No. 48, Iowa State University of Science and Technology Cooperative Extension Service, Ames, Iowa, Reprinted February 1993.

A polynucleotide of this embodiment (or subsequences thereof) can be obtained, for example, by using amplification primers which can be selectively hybridized and primer extended, under nucleic acid amplification conditions, to at least two sites within a polynucleotide of the present invention, or to two sites within the nucleic acid which flank and comprise a polynucleotide of the present invention, or to a site within a polynucleotide of the present invention and a site within the nucleic acid which comprises it. Methods for obtaining 5' and/or 3' ends of a vector insert are well known in the art. See, e.g., RACE (Rapid Amplification of Complementary Ends) as described in Frohman, M. A., in *PCR Protocols: A Guide to Methods and Applications*, Innis et al., eds. (Academic Press, Inc., San Diego), pp. 28–38 (1990)); see also, U.S. Pat. No. 5,470,722, and *Current Protocols in Molecular Biology*, Unit 15.6, Ausubel, et al., eds., Greene Publishing and Wiley-Interscience, New York (1995); Frohman and Martin, *Techniques* 1:165 (1989).

Optionally, the primers are complementary to a subsequence of the target nucleic acid which they amplify but may have a sequence identity ranging from about 85% to 99% relative to the polynucleotide sequence to which they are designed to anneal. As those skilled in the art will appreciate, the sites to which the primer pairs will selectively hybridize are chosen such that a single contiguous nucleic acid can be formed under the desired nucleic acid amplification conditions. The primer length in nucleotides is selected from the group of integers consisting of from at least 15 to 50. Thus, the primers can be at least 15, 18, 20, 25, 30, 40, or 50 nucleotides in length. Those of skill will recognize that a lengthened primer sequence can be employed to increase specificity of binding (i.e., annealing) to a target sequence. A non-annealing sequence at the 5' end of a primer (a "tail") can be added, for example, to introduce a cloning site at the terminal ends of the amplicon.

The amplification products can be translated using expression systems well known to those of skill in the art. The resulting translation products can be confirmed as polypeptides of the present invention by, for example, assaying for the appropriate catalytic activity (e.g., specific activity and/or substrate specificity), or verifying the presence of one or more linear epitopes which are specific to a polypeptide of the present invention. Methods for protein synthesis from PCR-derived templates are known in the art and available commercially. See, e.g., Amersham Life Sciences, Inc, Catalog '97, p.354.

C. Polynucleotides Which Selectively Hybridize to a Polynucleotide of SEQ ID NO:1, 2, 4, or 6

The present invention provides isolated nucleic acids comprising polynucleotides of the present invention, wherein the polynucleotides selectively hybridize, under selective hybridization conditions, to a polynucleotide of SEQ ID NO:1, 2, 4, or 6, or fragments or variants thereof as discussed above. Thus, the polynucleotides of this embodiment can be used for isolating, detecting, and/or quantifying nucleic acids comprising the polynucleotides of SEQ ID NO:1, 2, 4, or 6, or fragments or variants thereof. For example, polynucleotides of the present invention can be used to identify, isolate, or amplify partial or full-length clones in a deposited library. In some embodiments, the polynucleotides are genomic or cDNA sequences isolated or otherwise complementary to a cDNA from a dicot or monocot nucleic acid library. Exemplary species of monocots and dicots include, but are not limited to: maize, canola, soybean, cotton, wheat, sorghum, sunflower, alfalfa, oats, sugar cane, millet, barley, and rice. The cDNA library comprises at least 50% to 95% full-length sequences (for example, at least 50%, 60%, 70%, 80%, 90%, or 95% full-length sequences). The cDNA libraries can be normalized to increase the representation of rare sequences. See, e.g., U.S. Pat. No. 5,482,845.

D. Polynucleotides Having a Specific Sequence Identity with the Polynucleotides of SEQ ID NO:1, 2, 4, or 6

The present invention provides isolated nucleic acids comprising polynucleotides of the present invention, wherein the polynucleotides have a specified identity at the nucleotide level to a polynucleotide SEQ ID NO: 1, 2, 4, or 6, or fragments or variants thereof. Identity can be calculated using, for example, the BLAST or GAP algorithms under default conditions. The percentage of identity to a reference sequence is at least 50% and, rounded upwards to the nearest integer, can be expressed as an integer selected from the group of integers consisting of from 50 to 99. Thus, for example, the percentage of identity to a reference sequence can be at least 50%, 51%, 52%, 53%, 54%, 55%, 56%, 57%, 58%, 59%, 60%, 61%, 62%, 63%, 64%, 65%, 66%, 67%, 68%, 69%, 70%, 71% 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

E. Polynucleotides Encoding a Protein Having a Subsequence from a Prototype Polypeptide and Cross-Reactive to the Prototype Polypeptide The present invention provides isolated nucleic acids comprising polynucleotides of the present invention, wherein the polynucleotides encode a protein having a subsequence of contiguous amino acids from a prototype polypeptide of the present invention such as are provided in section (A), above. The subsequences of a nucleotide sequence may encode protein fragments that retain the biological activity of the native protein and hence have a defense-like activity. Such activity can include, for example, modulating disease resistance, modulating a plant defense response, modulating vesicle transport, modulating exocytosis, modulating membrane fusion, and the like. Assays to measure a modulation in disease resistance are discussed elsewhere herein. Methods to assay vesicular transport and membrane fusion are known in the art and include, for example, assaying for vesicular priming, docking, and fusion functions and kinetics. See, for example, Ungermann et al. (1996) *The EMBO Journal* 17:3269–3276 and Ungermann et al. (2000) *PNAS* 97:8889–8891, both of which are herein incorporated by reference. Further assays for modulating exocytosis and vesicular function include routine microscopy techniques that allow vesicular formation and location to determined. See, for example, Kwong et al. (2000) *Journal of Cell Science* 113: 2273–2284.

Alternatively, subsequences of a nucleotide sequence that are useful as hybridization probes generally do not encode fragment proteins retaining biological activity. Thus, subsequences of a nucleotide sequence may range from at least about 20 nucleotides, about 50 nucleotides, about 100 nucleotides, and up to the full-length nucleotide sequence encoding the proteins of the invention.

The length of contiguous amino acids from the prototype polypeptide is selected from the group of integers consisting of from at least 10 to the number of amino acids within the prototype sequence. Thus, for example, the polynucleotide can encode a polypeptide having a biologically active subsequence having at least 10, 15, 20, 25, 30, 35, 40, 45, 50, 60, 80, 100, 120, 140, 160, 180, or 185 contiguous amino acids from the prototype polypeptide. Further, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

Thus, a subsequence of SEQ ID NO: 1, 2, 4, or 6 may encode a biologically active portion of a defense-related protein, or it may be a fragment that can be used as a hybridization probe or PCR primer using methods disclosed below. A biologically active portion of a protein of the invention can be prepared by isolating a portion of one of the nucleotide sequences of the invention, expressing the encoded portion of the defense-related protein (e.g., by recombinant expression in vitro), and assessing the activity of the encoded portion of the defense-related protein. Nucleic acid molecules that are subsequences of the nucleotide sequence of the invention comprise at least 16, 20, 50, 75, 100, 150, 200, 250, 300, 350, 400, 450, 500, 550, 600, 650, 700, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100 nucleotides, or up to the number of nucleotides present in a full-length nucleotide sequence disclosed herein (for example, 3120, 1265, 1169, and 1178 nucleotides for SEQ ID NOS: 1, 2, 4, or 6, respectively]).

The proteins encoded by polynucleotides of this embodiment, when presented as an immunogen, elicit the production of polyclonal antibodies which specifically bind to a prototype polypeptide such as (but not limited to) a polypeptide encoded by the polynucleotide of sections (A) or (B) above. Generally, however, a protein encoded by a polynucleotide of this embodiment does not bind to antisera raised against the prototype polypeptide when the antisera has been fully immunosorbed with the prototype polypeptide. Methods of making and assaying for antibody binding specificity/affinity are well known in the art. Exemplary immunoassay formats include ELISA, competitive immunoassays, radioimmunoassays, Western blots, indirect immunofluorescent assays and the like.

In one assay method, fully immunosorbed and pooled antisera that is elicited to the prototype polypeptide can be used in a competitive binding assay to test the protein. The concentration of the prototype polypeptide required to inhibit 50% of the binding of the antisera to the prototype polypeptide is determined. If the amount of the protein required to inhibit binding is less than twice the amount of the prototype protein, then the protein is said to specifically bind to the antisera elicited to the immunogen. Accordingly, the proteins of the present invention embrace allelic variants, conservatively modified variants, and minor recombinant modifications to a prototype polypeptide.

A polynucleotide of the present invention optionally encodes a protein having a molecular weight of the non-glycosylated protein within 20% of the molecular weight of the full-length non-glycosylated polypeptides of the present invention. Molecular weight can be readily determined by SDS-PAGE under reducing conditions. Optionally, the molecular weight is within 15% of a full-length polypeptide of the present invention, more preferably within 10% or 5%, and most preferably within 3%, 2%, or 1% of a full-length polypeptide of the present invention.

Optionally, the polynucleotides of this embodiment will encode a protein having a specific enzymatic activity at least 50%, 60%, 70%, 80%, or 90% of a cellular extract comprising the native, endogenous full-length polypeptide of the present invention. Further, the proteins encoded by polynucleotides of this embodiment will optionally have a substantially similar affinity constant ($K_m$) and/or catalytic activity (i.e., the microscopic rate constant, $k_{cat}$) as the native endogenous, full-length protein. Those of skill in the art will recognize that $k_{cat}/K_m$ value determines the specificity for competing substrates and is often referred to as the specificity constant. Proteins of this embodiment can have a $k_{cat}/K_m$ value at least 10% of a full-length polypeptide of the present invention as determined using the endogenous substrate of that polypeptide. Optionally, the $k_{cat}/K_m$ value will be at least 20%, 30%, 40%, 50%, and most preferably at least 60%, 70%, 80%, 90%, or 95% the $k_{cat}/K_m$ value of the full-length polypeptide of the present invention. Determination of $k_{cat}$, $K_m$, and $k_{cat}/K_m$ can be determined by any number of means well known to those of skill in the art. For example, the initial rates (i.e., the first 5% or less of the reaction) can be determined using rapid mixing and sampling techniques (e.g., continuous-flow, stopped-flow, or rapid quenching techniques), flash photolysis, or relaxation methods (e.g., temperature jumps) in conjunction with such exemplary methods of measuring as spectrophotometry, spectrofluorimetry, nuclear magnetic resonance, or radioactive procedures. Kinetic values are conveniently obtained using a Lineweaver-Burk or Eadie-Hofstee plot.

F. Polynucleotides Complementary to the Polynucleotides of (A)–(E)

The present invention provides isolated nucleic acids comprising polynucleotides complementary to the polynucleotides of sections A–E, above. As those of skill in the art will recognize, complementary sequences base pair throughout the entirety of their length with the polynucleotides of sections (A)–(E) (i.e., have 100% sequence identity over their entire length). Complementary bases associate through hydrogen bonding in double stranded nucleic acids. For example, the following base pairs are complementary: guanine and cytosine; adenine and thymine; and adenine and uracil.

G. Polynucleotides that are Subsequences of the Polynucleotides of (A)–(F)

The present invention provides isolated nucleic acids comprising polynucleotides which comprise at least 15 contiguous bases from the polynucleotides of sections (A) (B), (C), (D), (E), or (F) (i.e., sections (A)–(F), as discussed above). A subsequence of a nucleotide sequence of the invention may encode a biologically active portion of a defense-related protein, or it may be a fragment that can be used as a hybridization probe or PCR primer using methods disclosed elsewhere herein. Subsequences of a nucleotide sequence of the invention that are useful as hybridization probes or PCR primers generally need not encode a biologically active portion of a defense-related protein.

The length of the polynucleotide is given as an integer selected from the group consisting of from at least 15 to the length of the nucleic acid sequence from which the polynucleotide is a subsequence of. Thus, for example, polynucleotides of the present invention are inclusive of polynucleotides comprising at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 85, 90, 95, 100, 110, 120, 130, 140, 150, 160, 170, 180, 190, 200, 210, 220, 230, 240, 250, 260, 270, 280, 290, 300, 350, 400, 450, 500, 550, 600, 650, 700, 750, 800, 850, 900, 950, or 1000 contiguous nucleotides in length from the polynucleotides of sections (A) through (F). Optionally, the number of such subsequences encoded by a polynucleotide of the instant embodiment can be any integer selected from the group consisting of from 1 to 1000, such as 2, 3, 4, or 5. The subsequences can be separated by any integer of nucleotides from 1 to the number of nucleotides in the sequence such as at least 5, 10, 15, 20, 25, 30, 35, 40, 45, 50, 75, 100, 200, 300, 400, 500, 600, 700, 800, 900, or 1000 nucleotides.

Subsequences can be made by in vitro synthetic, in vitro biosynthetic, or in vivo recombinant methods. In optional embodiments, subsequences can be made by nucleic acid amplification. For example, nucleic acid primers will be constructed to selectively hybridize to a sequence (or its complement) within, or co-extensive with, the coding region.

The subsequences of the present invention can comprise structural characteristics of the sequence from which it is derived. Alternatively, the subsequences can lack certain structural characteristics of the larger sequence from which it is derived such as a poly (A) tail. Optionally, a subsequence from a polynucleotide encoding a polypeptide having at least one linear epitope in common with a prototype polypeptide sequence as provided in (a), above, may encode an epitope in common with the prototype sequence. Alternatively, the subsequence may not encode an epitope in common with the prototype sequence but can be used to isolate the larger sequence by, for example, nucleic acid hybridization with the sequence from which it is derived. Subsequences can be used to modulate or detect gene expression by introducing into the subsequences compounds which bind, intercalate, cleave and/or crosslink to nucleic acids. Exemplary compounds include acridine, psoralen, phenanthroline, naphthoquinone, daunomycin or chloroethylaminoaryl conjugates.

H. Polynucleotides that are Variants of the Polynucleotides of (A)–(G)

By "variants" is intended substantially similar sequences. For nucleotide sequences, conservative variants include those sequences that, because of the degeneracy of the genetic code, encode the amino acid sequence of one of the defense-related polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis, but which still encode a defense-related protein of the invention. Generally, variants of a particular nucleotide sequence of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

I. Polynucleotides from a Full-length Enriched cDNA Library Having the Physico-Chemical Property of Selectively Hybridizing to a Polynucleotide of (A)–(H)

The present invention provides an isolated polynucleotide from a full-length enriched cDNA library having the physico-chemical property of selectively hybridizing to a polynucleotide of sections (A), (B), (C), (D), (E), (F), (G), or (H) as discussed above. Methods of constructing full-length enriched cDNA libraries are known in the art and discussed briefly below. The cDNA library comprises at least 50% to 95% full-length sequences (for example, at least 50%, 60%, 70%, 80%, 90%, or 95% full-length sequences). The cDNA library can be constructed from a variety of tissues from a monocot or dicot at a variety of developmental stages. Exemplary species include maize, wheat, rice, canola, soybean, cotton, sorghum, sunflower, alfalfa, oats, sugar cane, millet, barley, and rice. Methods of selectively hybridizing, under selective hybridization conditions, a polynucleotide from a full-length enriched library to a polynucleotide of the present invention are known to those of ordinary skill in the art. Any number of stringency conditions can be employed to allow for selective hybridization. In optional embodiments, the stringency allows for selective hybridization of sequences having at least 70%, 75%, 80%, 85%, 90%, 91%, 92%, 93%, 94%, 95%, 96%, 97%, 98%, 99%, up to 100% sequence identity over the length of the hybridized region. Full-length enriched cDNA libraries can be normalized to increase the representation of rare sequences.

J. Polynucleotide Products Made by a cDNA Isolation Process

The present invention provides an isolated polynucleotide made by the process of: 1) providing a full-length enriched nucleic acid library; and 2) selectively hybridizing the polynucleotide to a polynucleotide of sections (A), (B), (C), (D), (E), (F), (G), (H), or (I) as discussed above, and thereby isolating the polynucleotide from the nucleic acid library. Full-length enriched nucleic acid libraries are constructed and selective hybridization conditions are used, as discussed below. Such techniques, as well as nucleic acid purification procedures, are well known in the art. Purification can be conveniently accomplished using solid-phase methods; such methods are well known to those of skill in the art and kits are available from commercial suppliers such as Advanced Biotechnologies (Surrey, UK). For example, a polynucleotide of sections (A)–(H) can be immobilized to a solid support such as a membrane, bead, or particle. See, e.g., U.S. Pat. No. 5,667,976. The polynucleotide product of the present process is selectively hybridized to an immobilized polynucleotide and the solid support is subsequently isolated from non-hybridized polynucleotides by methods including, but not limited to, centrifugation, magnetic separation, filtration, electrophoresis, and the like.

Construction of Nucleic Acids

The isolated nucleic acids of the present invention can be made using standard recombinant methods, synthetic techniques, or combinations thereof. In some embodiments, the polynucleotides of the present invention will be cloned, amplified, or otherwise constructed from a monocot.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. A polynucleotide of the present invention can be attached to a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known and extensively described in the art. For a description of various nucleic acids see, for example, Stratagene Cloning Systems, Catalogs 1999 (La Jolla, Calif.); and, Amersham Life Sciences, Inc, Catalog '99 (Arlington Heights, Ill.).

A. Recombinant Methods for Constructing Nucleic Acids

The isolated nucleic acid compositions of this invention, such as RNA, cDNA, genomic DNA, or a synthetic analog or substitute or hybrid thereof, can be obtained from plant biological sources using any number of cloning methodologies known to those of skill in the art. In some embodiments, oligonucleotide probes which selectively hybridize under stringent conditions to the polynucleotides of the present invention are used to identify the desired sequence in a cDNA or genomic DNA library. Isolation of RNA and construction of cDNA and genomic libraries is well known to those of ordinary skill in the art. See, e.g., *Plant Molecular Biology: A Laboratory Manual*, Clark, ed., Springer-Verlag, Berlin (1997); and *Current Protocols in Molecular Biology*, Ausubel, et al., eds., Greene Publishing and Wiley-Interscience, New York (1995).

A1. Full-length Enriched cDNA Libraries

A number of cDNA synthesis protocols have been described which provide enriched fall-length cDNA libraries. Enriched full-length cDNA libraries are constructed to comprise at least 60%, or at least 70%, 80%, 90% or 95% full-length inserts among clones containing inserts. The length of insert in such libraries can be at least 2, 3, 4, 5, 6, 7, 8, 9, 10 or more kilobase pairs. Vectors to accommodate inserts of these sizes are known in the art and available commercially. See, e.g., Stratagene's lambda ZAP Express (cDNA cloning vector with 0 to 12 kb cloning capacity). An exemplary method of constructing a greater than 95% pure full-length cDNA library is described by Carninci et al., *Genomics*, 37:327–336 (1996). Other methods for producing full-length libraries are known in the art. See, e.g., Edery et al., *Mol. Cell Biol.*, 15(6):3363–3371 (1995); and, PCT Application WO 96/34981.

A2. Normalized or Subtracted cDNA Libraries

A non-normalized cDNA library represents the mRNA population of the tissue it was made from. Since unique clones are out-numbered by clones derived from highly expressed genes their isolation can be laborious. Normalization of a cDNA library is the process of creating a library in which each clone is more equally represented. Construction of normalized libraries is described in Ko, *Nucl. Acids. Res.*, 18(19):5705–5711 (1990); Patanjali et al., *Proc. Natl. Acad. U.S.A.*, 88:1943–1947 (1991); U.S. Pat. Nos. 5,482,685, 5,482,845, and 5,637,685. In an exemplary method described by Soares et al. (*Proc. Natl. Acad. Sci. U.S.A.* 91:9228–9232 (1994)), normalization resulted in reduction of the abundance of clones from a range of four orders of magnitude to a narrow range of only 1 order of magnitude.

Subtracted cDNA libraries are another means to increase the proportion of less abundant cDNA species. In this procedure, cDNA prepared from one pool of mRNA is depleted of sequences present in a second pool of mRNA by hybridization. The cDNA:mRNA hybrids are removed and the remaining un-hybridized cDNA pool is enriched for sequences unique to that pool. See Foote et al. in *Plant Molecular Biology: A Laboratory Manual*, Clark, ed., Springer-Verlag, Berlin (1997); Kho and Zarbl, Technique, 3(2):58–63 (1991); Sive and St. John, *Nucl. Acids Res.*, 16(22):10937 (1988); *Current Protocols in Molecular Biology*, Ausubel, et al., eds., Greene Publishing and Wiley-Interscience, New York (1995); and Swaroop et al., *Nucl. Acids Res.*, 19(17):4725–4730 (1991). cDNA subtraction kits are commercially available. See, e.g., PCR-Select (Clontech, Palo Alto, Calif.).

To construct genomic libraries, large segments of genomic DNA are generated by fragmentation, e.g., using restriction endonucleases, and are ligated with vector DNA to form concatemers that can be packaged into the appropriate vector. Methodologies to accomplish these ends, and sequencing methods to verify the sequence of nucleic acids are well known in the art. Examples of appropriate molecular biological techniques and instructions sufficient to direct persons of skill through many construction, cloning, and screening methodologies are found in Sambrook et al., *Molecular Cloning: A Laboratory Manual*, 2nd Ed., Cold Spring Harbor Laboratory Vols. 1–3 (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel, et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

The cDNA or genomic library can be screened using a probe based upon the sequence of a polynucleotide of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. The T4 gene 32 protein (Boehringer Mannheim) can be used to improve yield of long PCR products.

PCR-based screening methods have been described. Wilfinger et al. describe a PCR-based method in which the longest cDNA is identified in the first step so that incomplete clones can be eliminated from study. *BioTechniques*, 22(3):481–486 (1997). Such methods are particularly effective in combination with a full-length cDNA construction methodology, above.

B. Synthetic Methods for Constructing Nucleic Acids

The isolated nucleic acids of the present invention can also be prepared by direct chemical synthesis by methods such as the phosphotriester method of Narang et al., *Meth. Enzymol.* 68:90–99 (1979); the phosphodiester method of Brown et al., *Meth. Enzymol.* 68:109–151 (1979); the diethylphosphoramidite method of Beaucage et al., *Tetra. Lett.* 22:1859–1862 (1981); the solid phase phosphoramidite triester method described by Beaucage and Caruthers, *Tetra. Letts.* 22(20):1859–1862 (1981), e.g., using an automated synthesizer, e.g., as described in Needham-VanDevanter et al., *Nucleic Acids Res.*, 12:6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is best employed for sequences of about 100 bases or less, longer sequences may be obtained by the ligation of shorter sequences.

Recombinant Expression Cassettes

The present invention further provides recombinant expression cassettes comprising a nucleic acid of the present invention. A nucleic acid sequence coding for the desired polynucleotide of the present invention, for example a cDNA or a genomic sequence encoding a full length polypeptide of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plan expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A number of promoters can be used in the practice of the invention. A plant promoter fragment can be employed which will direct expression of a polynucleotide of the present invention in all tissues of a regenerated plant. Such promoters are referred to herein as "constitutive" promoters and are active under most environmental conditions and stated of development or cell differentiation. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter (Christensen et al. *Plant Mol. Biol.* 18: 675–689 (1992); Bruce et al., *Proc. Nat'l. Acad. Sci. U.S.A.* 86: 9692–9696 (1989)), the Smas promoter, the cinnamyl alcohol dehydrogenase promoter (U.S. Pat. No. 5,683,439), the Nos promoter, the pEmu promoter, the rubisco promoter, the GRP 1-8 promoter, the maize constitutive promoters described in PCT Publication No. WO 99/43797 which include the histone H2B, metallothionein, alpha-tubulin 3, elongation factor efla, ribosomal protein rps8, chlorophyll a/b binding protein, and glyceraldehyde-3-phosphate dehydrogenase promoters, and other transcription initiation regions from various plant genes known to those of skill.

Where low level expression is desired, weak promoters will be used. It is recognized that weak inducible promoters may be used. Additionally, either a weak constitutive or a weak tissue specific promoter may be used. Generally, by a "weak promoter" is intended a promoter that drives expression of a coding sequence at a low level. By low level is intended levels of about $\frac{1}{1000}$ transcripts to about $\frac{1}{100,000}$ transcripts to about $\frac{1}{500,000}$ transcripts. Alternatively, it is recognized that weak promoters also encompass promoters that are expressed in only a few cells and not in others to give a total low level of expression. Such weak constitutive promoters include, for example, the core promoter of the Rsyn7 (PCT Publication No. WO 97/44756), the core 35S CaMV promoter, and the like. Where a promoter is expressed at unacceptably high levels, portions of the promoter sequence can be deleted or modified to decrease expression levels. Additionally, to obtain a varied series in the level of expression, one can also make a set of transgenic plants containing the polynucleotides of the present invention with a strong constitutive promoter and then rank the transgenic plants according to the observed level of expression. The transgenic plants will show a variety of performances, from high expression to low expression. Factors such as chromosomal position effect, cosuppression, and the like will affect the expression of the polynucleotide.

Alternatively, the plant promoter can direct expression of a polynucleotide of the present invention under environmental control. Such promoters are referred to here as "inducible" promoters. Environmental conditions that may affect transcription by inducible promoters include pathogen attack, anaerobic conditions, or the presence of light. Examples of inducible promoters are the Adh1 promoter, which is inducible by hypoxia or cold stress, the Hsp70 promoter, which is inducible by heat stress, and the PPDK promoter, which is inducible by light. Examples of pathogen-inducible promoters include those from proteins which are induced following infection by a pathogen; e.g., PR proteins, SAR proteins, beta-1,3-glucanase, chitinase, etc. See, for example, Redolfi et al., *Meth J. Plant Pathol.* 89: 245–254 (1983); Uknes et al., *The Plant Cell* 4:45–656 (1992); Van Loon, *Plant Mol. Virol.* 4: 111–116 (1985); PCT Publication No. WO 99/43819.

Of interest are promoters that are expressed locally at or near the site of pathogen infection. See, for example, Marineau et al., *Plant Mol. Biol.* 9: 335–342 (1987); Matton et al., *Molecular Plant-Microbe Interactions* 2: 325–342 (1987); Somssich et al., *Proc. Nat'l. Acad. Sci. U.S.A.* 83: 2427–2430 (1986); Somssich et al., *Mol. Gen. Genetics* 2: 93–98 (1988); Yang, *Proc. Nat'l. Acad. Sci. U.S.A.* 93: 14972–14977. See also, Chen et al., *Plant J.* 10: 955–966 (1996); Zhang and Sing, *Proc. Nat'l. Acad. Sci. USA.* 91: 2507–2511 (1994); Warner et al., *Plant J.* 3: 191–201 (1993), and Siebertz et al., *Plant Cell* 1: 961–968 (1989). Of particular interest is the inducible promoter for the maize PRms gene, whose expression is induced by the pathogen *Fusarium moniliforme* (see, for example, Cordero et al., *Physiol. Mol. Plant Path.* 41: 189–200 (1992)).

Additionally, as pathogens find entry into plants through wounds or insect damage, a wound inducible promoter may be used in the constructs of the invention. Such wound inducible promoter include potato proteinase inhibitor (pin II) gene (Ryan, *Annu. Rev. Phytopath.* 28: 425–449 (1990); Duan et al., *Nat. Biotech.* 14: 494–498 (1996)); wun1 and wun2, U.S. Pat. No. 5,428,148; win1 and win2 (Stanford et al., *Mol. Gen. Genet.* 215: 200–208 (1989)); systemin (McGurl et al., *Science* 225: 1570–1573 (1992)); WIP1 (Rohmeier et al., *Plant Mol. Biol.* 22: 783–792 (1993); Eckelkamp et al., *FEB Letters* 323: 73–76 (1993)); MPI gene (Cordero et al., *The Plant J.* 6(2): 141–150(1994)); and the like.

Examples of promoters under developmental control include promoters that initiate transcription only, or preferentially, in certain tissues, such as leaves, roots, fruit, seeds, or flowers. Exemplary promoters include the anther-specific promoter 5126 (U.S. Pat. Nos. 5,689,049 and 5,689,051), glob-1 promoter, and gamma-zein promoter. An exemplary promoter for leaf- and stalk-preferred expression is MS8-15 (PCT Publication No. WO 98/00533). Examples of seed-preferred promoters include, but are not limited to, 27 kD gamma zein promoter and waxy promoter (Boronat et al., *Plant Sci.,* 47: 95–102 (1986); Reina et al., *Nucleic Acids Res.* 18(21): 6426 (1990); and Kloesgen et al., *Mol. Gen. Genet.* 203: 237–244 (1986)). Promoters that express in the embryo, pericarp, and endosperm are disclosed in U.S. patent application Ser. Nos. 60/097,233 (filed Aug. 20, 1998) and 60/098,230 (filed Aug. 28, 1998). The operation of a promoter may also vary depending on its location in the genome. Thus, a developmentally-regulated promoter may become fully or partially constitutive in certain locations. A developmentally-regulated promoter can also be modified, if necessary, for weak expression.

Both heterologous and non-heterologous (i.e., endogenous) promoters can be employed to direct expression of the nucleic acids of the present invention. These promoters can also be used, for example, in recombinant expression cassettes to drive expression of antisense nucleic acids to reduce, increase, or alter concentration and/or composition of the proteins of the present invention in a desired tissue. Thus, in some embodiments, the nucleic acid construct will comprise a promoter functional in a plant cell, such as in *Zea mays*, operably linked to a polynucleotide of the present invention. Promoters useful in these embodiments include the endogenous promoters driving expression of a polypeptide of the present invention.

In some embodiments, isolated nucleic acids which serve as promoter or enhancer elements can be introduced in the appropriate position (generally upstream) of a non-heterologous form of a polynucleotide of the present invention so as to up- or down-regulate expression of a polynucleotide of the present invention. For example, endogenous promoters can be altered in vivo by mutation, deletion, and/or substitution (see, Kmiec, U.S. Pat. No. 5,565,350; Zarling et al., PCT/US93/03868), or isolated promoters can be introduced into a plant cell in the proper orientation and distance from a gene of the present invention so as to control the expression of the gene. Gene expression can be modulated under conditions suitable for plant growth so as to alter the total concentration and/or alter the composition of the polypeptides of the present invention in plant cell. Thus, the present invention provides compositions comprising heterologous promoters and/or enhancers operably linked to a native, endogenous (i.e., non-heterologous) form of a polynucleotide of the present invention, and methods for making the same.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene or from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. See Buchman and Berg, *Mol. Cell Biol.* 8:4395–4405 (1988); Callis et al., *Genes Dev.* 1:1183–1200 (1987). Such intron enhancement of gene expression is typically greatest when placed near the 5' end of the transcription unit. Use of the maize Adh1-S introns 1, 2, and 6 and the Bronze-1 intron are known in the art. See generally, *The Maize Handbook*, Chapter 116, Freeling and Walbot, eds., Springer, N.Y.( 1994).

The vector comprising the sequences from a polynucleotide of the present invention will typically comprise a marker gene which confers a selectable phenotype on plant cells. Usually the selectable marker gene will encode antibiotic resistance, with suitable marker genes including those coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS) (in particular, ALS mutant genes conferring resistance to sulfonylurea-type herbicides, for example, the S4 and/or Hra mutations), genes coding for resistance to herbicides (such as phosphinothricin or basta) which act to inhibit action of glutamine synthase, (e.g., the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfaron.

Typical vectors useful for expression of genes in higher plants are well known in the art and include vectors derived from the tumor-induced (Ti) plasmid of *Agrobacterium tumefaciens* (described by Rogers et al., *Meth. In Enzymol.* 153:253–277 (1987)). These vectors are known as "plant-integrating vectors" because upon transformation into a host plant cell, the vectors integrate a portion of vector DNA into the genome of the cell. Exemplary *A. tumefaciens* vectors useful herein are plasmids pKYLX6 and pKYLX7 as described in Schardl et al., Gene 61:1–11 (1987) and Berger et al., *Proc. Nat'l. Acad. Sci. U.S.A.*, 86:8402–8406 (1989). Another useful vector herein is plasmid pBI101.2, available from Clontech Laboratories (Palo Alto, Calif.).

A polynucleotide of the present invention can be expressed in either sense or anti-sense orientation as desired.

It will be appreciated that control of gene expression in either sense or anti-sense orientation can have a direct impact on the observable plant characteristics. Antisense technology can be conveniently used to inhibit gene expression in plants. To accomplish this, a nucleic acid segment from the desired gene is cloned and operably linked to a promoter such that the anti-sense strand of RNA will be transcribed. The construct is then transformed into plants and the antisense strand of RNA is produced. In plant cells, it has been shown that antisense RNA inhibits gene expression by preventing the accumulation of mRNA which encodes the enzyme of interest. See, e.g., Sheehy et al., *Proc. Nat'l. Acad. Sci U.S.A.* 85:8805–8809 (1988) and Hiatt et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes, see Napoli et al., *The Plant Cell* 2:279–289 (1990) and U.S. Pat. No. 5,034,323.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al., *Nature* 334:585–591 (1988).

A variety of cross-linking agents, alkylating agents and radical-generating species as pendant groups on polynucleotides of the present invention can be used to bind, label, detect, and/or cleave nucleic acids. For example, Vlassov et al. (*Nucleic Acids Res.* (1986) 14:4065–4076) describe covalent bonding of a single-stranded DNA fragment with alkylating derivatives of nucleotides complementary to target sequences. A report of similar work by the same group is: Knorre et al., *Biochimie* 67:785–789 (1985). Iverson and Dervan also showed sequence-specific cleavage of single-stranded DNA mediated by incorporation of a modified nucleotide which was capable of activating cleavage (*J. Am. Chem. Soc.* (1987) 109:1241–1243). Meyer et al. (*J. Am. Chem. Soc.* 111:8517–8519 (1989)) effect covalent crosslinking to a target nucleotide using an alkylating agent complementary to the single-stranded target nucleotide sequence. A photoactivated crosslinking to single-stranded oligonucleotides meditated by psoralen was disclosed by Lee et al., *Biochemistry* 27:3197–3203 (1988). Use of crosslinking in triple-helix forming probes was also disclosed by Home et al. (*J. Am. Chem. Soc.* 112:2435–2437 (1990)). Use of N4, N4-ethanocytosine as an alkylating agent to crosslink to single-stranded oligonucleotides has also been described by Webb and Matteucci, (*J. Am. Chem. Soc.* 108:2764–2765 (1986)); Nucleic Acids Res. 14:7661–7674 (1986); Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672,593; 5,484,908; 5,256,648; and 5,681,941.

Proteins

Also provided are proteins and polypeptides. In one embodiment, the proteins and polypeptides provided comprise the *Zea mays* SNAP25 protein having an amino acid sequence as set forth in SEQ ID NO:3; the *Oryza sativa* SNAP25 protein having an amino acid sequence as set forth in SEQ ID NO:5; and the *Triticum aestivum* SNAP25 protein having an amino acid sequence as set forth in SEQ ID NO:7.

In another aspect, the present invention relates to an isolated protein selected from the group consisting of: (a) a polypeptide comprising at least 25 contiguous amino acids of SEQ ID NO:3, 5, or 7; (b) a polypeptide which is a plant SNAP25; (c) a polypeptide comprising at least 55% sequence identity to SEQ ID NO:3, 5, or 7; (d) a polypeptide encoded by a nucleic acid of the present invention; (e) a polypeptide characterized by SEQ ID NO:3, 5, or 7; and (f) a conservatively modified variant of SEQ ID NO:3, 5, or 7.

The isolated proteins of the present invention comprise a polypeptide having at least 10 amino acids encoded by any one of the polynucleotides of the present invention as discussed more fully, above, or polypeptides which are conservatively modified variants thereof. The proteins of the present invention or variants thereof can comprise any number of contiguous amino acid residues from a polypeptide of the present invention, wherein that number is selected from the group of integers consisting of from 10 to the number of residues in a full-length polypeptide of the present invention. Optionally, this subsequence of contiguous amino acids is at least 15, 16, 17, 18, 19, 20, 21, 22, 23, 24, 25, 26, 27, 28, 29, 30, 31, 32, 33, 34, 35, 37, 38, 39, or 40 amino acids in length, often at least 50, 55, 60, 65, 70, 75, 80, 85, 90, 95, 100, 120, 140, 160, 180, 200, 220, 240, 260, 280, amino acids in length.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, defense-related activity as described herein. Such variants may result from, for example, genetic polymorphism or from human manipulation. Biologically active variants of a native defense-related protein of the invention will have at least about 40%, 50%, 60%, 65%, 70%, generally at least about 75%, 80%, 85%, preferably at least about 90%, 91%, 92%, 93%, 94%, 95%, 96%, 97% and more preferably at least about 98%, 99% or more sequence identity to the amino acid sequence for the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

As those of skill will appreciate, the present invention includes catalytically active polypeptides of the present invention (i.e., enzymes). Catalytically active polypeptides have a specific activity of at least 20%, 30%, or 40%, and preferably at least 50%, 60%, or 70%, and most preferably at least 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art.

Generally, the proteins of the present invention will, when presented as an immunogen, elicit production of an antibody specifically reactive to a polypeptide of the present invention. Further, the proteins of the present invention will not bind to antisera raised against a polypeptide of the present invention which has been fully immunosorbed with the same polypeptide. Immunoassays for determining binding are well known to those of skill in the art. A preferred immunoassay is a competitive immunoassay as discussed infra. Thus, the proteins of the present invention can be employed as immunogens for constructing antibodies immunoreactive to a protein of the present invention for such exemplary utilities as immunoassays or protein purification techniques.

The proteins of the invention may be altered in various ways including amino acid substitutions, deletions, truncations, and insertions. Methods for such manipulations are generally known in the art. For example, amino acid sequence variants of the proteins pf the invention can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferable.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired defense-related activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequence[s] encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by modulating a plant-defense response; modulating disease resistance; modulation vesicle transport; exocytosis; membrane fusion; and the like. More details regarding routine assays to measure such activity are described elsewhere herein.

As discussed elsewhere herein, variant nucleotide sequences and proteins also encompass sequences and proteins derived from a mutagenic and recombinogenic procedure such as DNA shuffling. With such a procedure, one or more different coding sequence of the invention can be manipulated to create a new defense-related sequence possessing the desired properties. In this manner, libraries of recombinant polynucleotides are generated from a population of related sequence polynucleotides comprising sequence regions that have substantial sequence identity and can be homologously recombined in vitro or in vivo.

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition. (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or regulatable), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high-level expression of a cloned gene, it is desirable to construct expression vectors which contain, at the minimum, a strong promoter to direct transcription, a ribosome binding site for translational initiation, and a transcription/translation terminator. One of skill would recognize that modifications could be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located purification sequences. Restriction sites or termination codons can also be introduced.

A. Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang et al, *Nature* 198:1056 (1977)), the tryptophan (trp) promoter system (Goeddel et al., *Nucleic Acids Res.* 8:4057 (1980)) and the lambda-derived P L promoter and N-gene ribosome binding site (Shimatake et al., *Nature* 292:128(1981)). The inclusion of selection markers in DNA vectors transfected in *E. coli*. is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using Bacillus sp. and Salmonella (Palva et al., *Gene* 22:229–235 (1983); Mosbach et al., *Nature* 302:543–545 (1983)).

B. Expression in Eukaryotes

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman et al., *Methods in Yeast Genetics*, Cold Spring Harbor Laboratory (1982), is a well-recognized work describing the various methods available to produce the protein in yeast. Two widely utilized yeasts for production of eukaryotic proteins are *Saccharomyces cerevisiae* and *Pichia pastoris*. Vectors, strains, and protocols for expression in Saccharomyces and Pichia are known in the art and available from commercial suppliers (e.g., Invitrogen). Suitable vectors usually have expression control sequences such as promoters (including 3-phosphoglycerate kinase or alcohol oxidase) and an origin of replication, termination sequences and the like as desired.

A protein of the present invention, once expressed, can be isolated from yeast by lysing the cells and applying standard protein isolation techniques to the lists. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Illustrative cell cultures useful for the production of the peptides are mammalian cells. Mammalian cell systems often will be in the form of minelayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen et al., *Immunol. Rev.* 89:49 (1986)), and necessary processing information sites, such as ribosome binding sites, RNA splice sites, polyadenylation sites (e.g., an SV40 large T-Ag poly-A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and Drosophila cell lines such as a Schneider cell line (see Schneider, *J. Embryol. Exp. Morphol.* 27:353–365 (1987).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague et al., *J. Virol.* 45:773–781 (1983)). Additionally, gene sequences to control replication in the host cell may be incorporated into the vector such as those found in bovine papilloma virus type-vectors. See Saveria-Campo, "Bovine Papilloma Virus DNA, a Eukaryotic Cloning Vector," pp. 213–238 in *DNA Cloning Vol. II: a Practical Approach*, Glover, ed., IRL Press, Arlington, Va. (1985).

Transfection/Transformation of Cells

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method which provides for effective transformation/transfection may be employed.

A. Plant Transformation

The genes of the present invention can be used to transform any plant. In this manner, genetically modified plants, plant cells, plant tissue, seed, and the like can be obtained. Transformation protocols may vary depending on the type of plant cell, i.e., monocot or dicot, targeted for transformation. Suitable methods of transforming plant cells include microinjection (Crossway et al., BioTechniques 4: 320–334 (1986)), electroporation (Riggs et al., *Proc. Natl. Acad. Sci. U.S.A.* 83: 5602–5606 (1986)), Agrobacterium mediated transformation (Hinchee et al., (1988) *Biotechnology* 6: 915–921 (1988); U.S. Pat. No. 5,981,840 (maize); U.S. Pat. No. 5,932,782 (sunflower), European Patent No. 0486233 (sunflower); PCT Application No. WO 98/49332 (sorghum)), direct gene transfer (Paszkowski et al., *EMBO J.* 3: 2717–2722 (1984)), and ballistic particle acceleration. See, for example, Sanford et al., U.S. Pat. No. 4,945,050; Tomes et al., "Direct DNA Transfer into Intact Plant Cells via Microprojectile Bombardment," in *Plant Cell, Tissue and Organ Culture: Fundamental Methods*, Gamborg and Phillips, eds., Springer-Verlag, Berlin (1995); McCabe et al., *Biotechnology* 6:923–926 (1988)); U.S. Pat. No. 5,990,387 (maize), U.S. Pat. No. 5,886,244 (maize); U.S. Pat. No. 5,322,783 (sorghum). Also see, Weissinger et al., *Ann. Rev. Genet.* 22: 421–477 (1988); Sanford et al., *Particulate Science and Technology* 5: 27–37 (1987) (onion); Christou et al., *Plant Physiol.* 87: 671–674 (1988)(soybean); McCabe et al., *Bio/Technology* 6: 923–926 (1988) (soybean); Datta et al., *Biotechnology* 8: 736–740 (1990) (rice); Klein et al, *Proc. Natl. Acad. Sci. USA*. 85: 4305–4309 (1988) (maize); Klein et al., *Biotechnology* 6: 559–563 (1988) (maize); Tomes et al., "Direct DNA Transfer into Intact Plant Cells via Microprojectile Bombardment" in Gamborg and Phillips, eds., *Plant Cell, Tissue and Organ Culture: Fundamental Methods*, Springer-Verlag, Berlin (1995) (maize); Klein et al., *Plant Physiol.* 91: 440–444 (1988) (maize), Fromm et al., *Biotechnology* 8: 833–839 (1990) (maize); Hooykaas-Van Slogteren & Hooykaas *Nature (London)* 311: 763–764 (1984); Bytebier et al., *Proc. Natl. Acad. Sci. U.S.A.* 84: 5345–5349 (1987) (Liliaceae); De Wet et al., pp. 197–209 in *The Experimental Manipulation of Ovule Tissues*, Chapman et al., eds., Longman, N.Y. (1985) (pollen); Kaeppler et al., *Plant Cell Reports* 9: 415–418 (1990); and Kaeppler et al., (1992) *Theor. Appl. Genet.* 84: 560–566 (whisker-meditated transformation); D'Halluin et al., *Plant Cell* 4: 1495–1505 (1992) (electroporation); Li et al., *Plant Cell Reports* 12: 250–255 (1993) and Christou and Ford, *Annals of Botany* 75: 745–750 (1995) (maize via *Agrobacterium tumefaciens*).

The cells which have been transformed may be grown into plants in accordance with conventional methods. See, for example, McCormick et al., *Plant Cell Reports* 5: 81–84 (1986). These plants may then be pollinated with either the same transformed strain or different strains and the resulting progeny examined to identify a hybrid having the desired phenotypic characteristic(s). Two or more generations may be grown to ensure that the subject phenotypic characteristic is stably maintained and inherited; seeds of these generations may be harvested to ensure that the desired phenotype or other property has been achieved. One of skill will recognize that after the recombinant expression cassette is stably incorporated in transgenic plants and confirmed to be operable, it can be introduced into other plants by sexual crossing. Any of number of standard breeding techniques can be used, depending upon the species to be crossed.

In vegetatively propagated crops, mature transgenic plants can be propagated by the taking of cuttings or by tissue culture techniques to produce multiple identical plants. In this manner, desirable transgenics may be selected and new varieties may be obtained and propagated vegetatively for commercial use. In seed propagated crops, mature transgenic plants can be self-crossed to produce a homozygous inbred plant. The inbred plant produces seed containing the newly-introduced heterologous nucleic acid. These seeds can be grown to produce plants that would exhibit the desired phenotype.

Parts obtained from the regenerated plant, such as flowers, seeds, leaves, branches, fruit, and the like are included in the invention, provided that these parts comprise cells comprising an introduced nucleic acid of the present invention. Progeny, variants, and mutants of the regenerated plants are also included within the scope of the invention, provided that these parts comprise introduced nucleic acid sequences.

In some embodiments, a transgenic plant is homozygous for the added heterologous nucleic acid; i.e., a transgenic plant contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating the seed produced and analyzing the resulting plants produced for homozygosity. Such analysis may be molecular (e.g., by hybridization analysis) or phenotypic (e.g., for altered expression of a polynucleotide of the present invention relative to a control plant such as a native and/or non-transgenic plant). Backcrossing to a parental plant and out-crossing with a non-transgenic plant are also contemplated.

B. Transfection of Prokaryotes, Lower Eukaryotes, and Animal Cells

Animal and lower eukaryotic host cells (e.g., yeast) are competent or rendered competent for transfection by various means. There are several well-known methods of introducing DNA into animal cells. These include calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. See Kuchler, *Biochemical Methods in Cell Culture and Virology*, Dowden, Hutchinson and Ross, Inc (1997).

Modulating Polypeptide Levels and/or Composition

The present invention further provides a method for modulating (i.e., increasing or decreasing) the concentration or composition of the polypeptides of the present invention in a plant or part thereof. Increasing or decreasing the concentration and/or the composition (i.e., the ratio of the polypeptides of the present invention) in a plant can effect modulation. The method comprises: 1) introducing into a plant cell a recombinant expression cassette comprising a polynucleotide of the present invention as described above to obtain a transformed plant cell, 2) culturing the transformed plant cell under appropriate growing conditions, and 3) inducing or repressing expression of a polynucleotide of the present invention in the plant for a time sufficient to modulate concentration and/or composition of the encoded polypeptide in the plant or plant part.

In some embodiments, the content and/or composition of polypeptides of the present invention in a plant may be modulated by altering, in vivo or in vitro, the promoter of a gene to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868. In some embodiments, an isolated nucleic acid (e.g., a vector) comprising a promoter sequence is transfected into a plant cell. Subsequently, a plant cell comprising the promoter operably linked to a polynucleotide of the present invention is selected by means known to those of skill in the art, such as (but not limited to) Southern blot, DNA sequencing, or PCR analysis using primers specific to the promoter and to the gene and detecting amplicons produced therefrom. A plant or plant part altered or modified by the foregoing embodiments is grown under appropriate conditions for a time sufficient to modulate the concentration and/or composition of polypeptides of the present invention in the plant. Appropriate conditions for plant growth are well known in the art and discussed briefly, supra.

In general, concentration or composition of a particular polypeptide is increased or decreased by at least 5%, 10%, 20%, 30%, 40%, 50%, 60%, 70%, 80%, or 90% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation (as discussed in greater detail elsewhere herein). Induction of expression of a polynucleotide of the present invention can also be controlled by exogenous administration of an effective amount of inducing compound. Inducible promoters and inducing compounds which activate expression from these promoters are well known in the art. In certain embodiments, the polypeptides of the present invention are modulated in monocots, particularly maize.

Molecular Markers

The present invention provides a method of genotyping a plant comprising a polynucleotide of the present invention. Optionally, the plant is a monocot, such as maize or sorghum. Genotyping provides a means of distinguishing homologs of a chromosome pair and can be used to differentiate segregants in a plant population. Molecular marker methods can be used for phylogenetic studies, for characterizing genetic relationships among crop varieties, for identifying crosses or somatic hybrids, for localizing chromosomal segments affecting monogenic traits, for map based cloning, and for the study of quantitative inheritance. See, e.g., *Plant Molecular Biology: A Laboratory Manual*, Chapter 7, Clark, ed., Springer-Verlag, Berlin (1997). For molecular marker methods, see generally, Paterson, "The DNA Revolution," pp. 7–21 (Chapter 2) in *Genome Mapping in Plants*, Paterson, ed., Academic Press/R.G. Lands Company, Austin, Tex. (1996).

The particular method of genotyping in the present invention may employ any number of molecular marker analytic techniques such as, but not limited to, restriction fragment length polymorphisms (RFLPs). RFLPs are the product of allelic differences between DNA restriction fragments resulting from nucleotide sequence variability. As is well known to those of skill in the art, RFLPs are typically detected by extraction of genomic DNA and digestion with a restriction enzyme. Generally, the resulting fragments are separated according to size and hybridized with a probe, such as a single copy probe. Restriction fragments from homologous chromosomes are revealed. Differences in fragment size among alleles represent an RFLP. Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a gene of the present invention, whether that gene is in its native chromosomal location or has been introduced into another chromosomal location by some means, such as genetic transformation.

In the present invention, the nucleic acid probes employed for molecular marker mapping of plant nuclear genomes selectively hybridize under selective hybridization conditions to a gene encoding a polynucleotide of the present invention. In certain embodiments, the probes are selected from polynucleotides of the present invention. Typically, these probes are cDNA probes or restriction-enzyme-treated genomic clones (e.g., clones digested with the enzyme PstI). The length of the probes is discussed in greater detail supra but is typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in the haploid chromosome complement. Some exemplary restriction enzymes employed in RFLP mapping are EcoRI, EcoRV, and SstI. As used herein, the term "restriction enzyme" includes reference to a composition that recognizes and, alone or in conjunction with another composition, cleaves at a specific nucleotide sequence.

The method of detecting an RFLP comprises the steps of: (a) digesting genomic DNA of a plant with a restriction enzyme; (b) hybridizing a nucleic acid probe under selective hybridization conditions to a sequence of a polynucleotide present in said genomic DNA; (c) detecting thereby a RFLP. Other methods of differentiating polymorphic (allelic) variants of polynucleotides of the present invention can be had by utilizing molecular marker techniques well known to those of skill in the art including such techniques as: 1) single stranded conformation analysis (SSCA); 2) denaturing gradient gel electrophoresis (DGGE); 3) RNAse protection assays; 4) selective hybridization to allele-specific oligonucleotides (ASOs); 5) detection by proteins which recognize nucleotide mismatches, such as the *E. coli* mutS protein; and 6)allele-specific PCR. Other approaches based on the detection of mismatches between the two complementary DNA strands include clamped denaturing gel electrophoresis (CDGE), heteroduplex analysis (HA), and chemical mismatch cleavage (CMC). Thus, the present invention further provides a method of genotyping comprising the steps of contacting, under stringent hybridization conditions, a sample suspected of comprising a polynucleotide of the present invention with a nucleic acid probe. Generally, the sample is a plant sample, for example, a sample suspected of comprising a maize polynucleotide of the present invention (e.g., a gene or mRNA). The nucleic acid probe selectively hybridizes under stringent conditions to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In certain embodiments, the nucleic acid probe comprises a polynucleotide of the present invention.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, *Nucleic Acids Res.* 15:8125 (1987)) and the 7-methylguanosine cap structure (Drummond et al., *Nucleic Acids Res.* 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, *Nucleic Acids Res.* 15:8125 (1987); Rao et al., *Mol. Cell. Biol.* 8:284 (1988)). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host. For example, altered codon usage can be employed to optimize the codon usage in a heterologous sequence for expression in maize. Codon usage in the coding regions of the polynucleotides of the present invention can be analyzed statistically using commercially available software packages such as "Codon Preference," available from the University of Wisconsin Genetics Computer Group (see Devereaux et al., *Nucleic Acids Res.* 12:387–395 (1984)) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50, or 100.

Novel Sequence Construction and Sequence Shuffling

The present invention provides methods and compositions for creating novel sequences and for sequence shuffling, and compositions resulting therefrom. Novel sequences may be created by combining subsequences of the sequences of the invention, either with each other or with unrelated sequences, to create a sequence having novel properties. For example, a nucleotide sequence encoding a protein domain responsible for nuclear localization may be added to a sequence encoding a protein which is normally localized in the cytoplasm; the novel protein encoded by the novel nucleotide sequence may then be localized in the nucleus rather than the cytoplasm of a cell expressing it. Sequence shuffling is described in PCT Publication No. WO 96/19256. See also, Zhang et al., *Proc. Nat'l. Acad. Sci.* *U.S.A.* 94:4504–4509 (1997). Generally, sequence shuffling provides a means for generating libraries of polynucleotides having a desired characteristic, which may be identified by selection or screening. In sequence shuffling, libraries of recombinant polynucleotides are generated from a population of related sequence polynucleotides. These polynucleotides comprise sequence regions which have substantial identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be a decreased $K_m$ and/or increased $K_{cat}$ over the wild-type protein as provided herein. In other embodiments, a protein or polynucleotide generated from sequence shuffling will have a ligand binding affinity greater than the non-shuffled wild-type polynucleotide. The increase in such properties can be at least 110%, 120%, 130%, 140%, or at least 150% of the wild-type value.

For example, using this approach, sequence motifs encoding a domain of interest may be shuffled between the nucleotide sequences of the invention and other known genes to obtain a new gene encoding a protein with an improved property of interest, such as a broader spectrum of pathogen resistance. It is understood that, having described the polynucleotide and polypeptide sequences of the present invention, one of skill will recognize that domains having properties of interest may be identified and isolated from these sequences, and that these domains may be used to confer their properties of interest on sequences containing them or they may be shuffled to create domains having improved properties of interest. Likewise, sequences corresponding to regulatory motifs, such as specific cis-acting elements within the promoter sequences of the invention may be used to confer their attributes to sequences containing them or they may be shuffled to create improved regulatory functions, such as increased pathogen inducibility. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

Generic and Consensus Sequences

Polynucleotides and polypeptides of the present invention further include those having: (a) a generic sequence of at least two homologous polynucleotides or polypeptides, respectively, of the present invention; and (b) a consensus sequence of at least three homologous polynucleotides or polypeptides, respectively, of the present invention. The generic sequence of the present invention comprises each species of polypeptide or polynucleotide embraced by the generic polypeptide or polynucleotide sequence, respectively. The individual species encompassed by a polynucleotide having an amino acid or nucleic acid consensus sequence can be used to generate antibodies or produce nucleic acid probes or primers to screen for homologs in other species, genera, families, orders, classes, phyla, or kingdoms. For example, a polynucleotide having a consensus sequence from a gene family of *Zea mays* can be used to generate antibody or nucleic acid probes or primers to other Gramineae species such as wheat, rice, or sorghum. Alternatively, a polynucleotide having a consensus sequence generated from orthologous genes can be used to identify or isolate orthologs of other taxa. Typically, a polypeptide or polynucleotide having a consensus sequence will be at least 9, 10, 15, 20, 25, 30, or 40 amino acids in length, or 20, 30, 40, 50, 100, or 150 nucleotides in length, respectively. As those of skill in the art are aware, to form an optimal consensus sequence, a conservative amino acid substitution can be used for amino acids which differ among aligned sequences but are from the same conservative amino acid substitution group as discussed above. Optionally, no more than 1 or 2 conservative amino acids are substituted for each 10 amino acid length of consensus sequence.

Similar sequences used for generation of a consensus or generic sequence include any number and combination of allelic variants of the same gene or orthologous or paralogous sequence as provided herein. Optionally, similar sequences used in generating a consensus or generic sequence are identified using the BLAST algorithm's smallest sum probability (P(N)). Various suppliers of sequence-analysis software are listed in chapter 7 of *Current Protocols in Molecular Biology* (Supplement 30), Ausubel et al., eds., Greene Publishing Associates, Inc. and John Wiley & Sons, Inc. A polynucleotide sequence is considered similar to a reference sequence if the smallest sum probability in a comparison of the test nucleic acid to the reference nucleic acid is less then about 0.1, more preferably less than about 0.01, or 0.001, and most preferably less than about 0.0001, or 0.00001. Similar polynucleotides can be aligned and a consensus or generic sequence generated using multiple sequence alignment software available from a number of commercial suppliers such as the Genetics Computer Group's (Madison, Wis.) PILEUP software, Vector NTI's (North Bethesda, Md.) ALIGNX, or Genecode's (Ann Arbor, Mich.) SEQUENCER. Conveniently, default parameters of such software can be used to generate consensus or generic sequences.

The following examples are included for purposes of illustration rather than limitation.

EXPERIMENTAL

EXAMPLE 1

Characterization and Cloning of Rust Mimic-1(Rm1) in Maize

In maize, certain gene mutations cause necrotic lesions at various plant developmental stages without any obvious stress, injury or disease pathogen. These are called "disease lesion mimic mutations" because the lesions are often similar in appearance to some of the known diseases of maize. The rust mimic-1 mutation (rm1) is so named because of its similarity in appearance to 4–6 week old plants with pustules from rust, a fungal disease of maize. Lesions caused by rm1 are characterized by the formation of reddish-brown necrotic spots and patches on leaf blades. These symptoms are very severe in the area of veins and the leaf sheath. After a rm1 plant flowers, browning has also been observed to proceed internally from the node in a basipetal manner, causing severe necrosis on the lowermost internodes of the stalk. This mutation is a recessive, single-gene mutation that was first observed in a Mutator F2 population. The mutant line was genetically advanced for co-segregation analysis by crossing with B73 and A632 inbred lines, a couple of times, followed by self-pollination of a number of progeny plants.

A. Cloning

Co-segregation analysis was performed on BC2 F2 plants. DNA from mutants (rm1/rm1), hetrozygotes (+/rm1), and wild-type sibs (+/+) was isolated, restriction digested, and hybridized with a DNA probe from each of the nine Mu elements. A 5.8 kb Mu1-hybridizing BamHI restriction fragment, which also hybridized to a Mu1-specific probe, was found to co-segregate with the mutant phenotype in about 80 plants. This Mu2-hybridizing band was isolated from a sub-genomic library prepared from rm1 plants and cloned into the Zap Express vector (Stratagene). The rm15.8 kb BamHI clone was subcloned as a 1.7 kb SacI fragment and a 2.2 kb SacI fragment in pBSK+ (Stratagene); the rest of the rm1 fragment (1.9 kb) was recircularized. These subclones were end-sequenced and a 0.7 kb BamHI-SacII fragment (comprising the flanking DNA up to the site of the Mu2 insertion) was used as a probe to clone a 12.8 kb genomic clone from the B73 library. These clones were restriction mapped and the Mu2 insertion site identified.

B. Isolation of cDNA

Sequence information from these subclones was compiled and homology searches were performed with public and proprietary databases. Two full-length ESTs showing sequence matches to the rm1 genomic sequence were identified from proprietary databases. These ESTs were acquired and sequenced, and the sequence information of the mutant allele, B73 genomic clone, and ESTs were compared to construct the native structure of the Rm1 gene (sequence set forth in SEQ ID NO:1; structure diagrammed in FIG. 2). The Rm1 gene in maize has five exons and four introns, and an additional intron is present in the 5' untranslated region of the gene. The promoter is flanked by a Cin element at its upstream end (FIG. 2.) The full length Rm1 cDNA is about 1.2 kb in length (set forth in SEQ ID NO:2); the predicted amino acid sequence is set forth in size of protein SEQ ID NO:3.

A homology search of the public GenBank database detected a homologous sequence from *Arabidopsis thaliana* (SEQ ID NO:9) (GenBank Accession No. X92420), set forth in SEQ ID NO:8 which was annotated to suggest that it encodes a SNAP25 protein. Additional SNAP sequences from rice and wheat were identified. The maize Rm1 predicted protein sequence has 80.7%, 76.9%, and 52.1% identity at the amino acid level with rice SNAP25, wheat SNAP25, and Arabidopsis SNAP25 proteins, respectively, throughout their entire length. The nucleotide identity between the maize Rm1 coding region and the corresponding cDNAs from wheat, rice, and Arabidopsis is 83.9%, 78.1% and 62%, respectively.

C. Mapping

Figure 3:
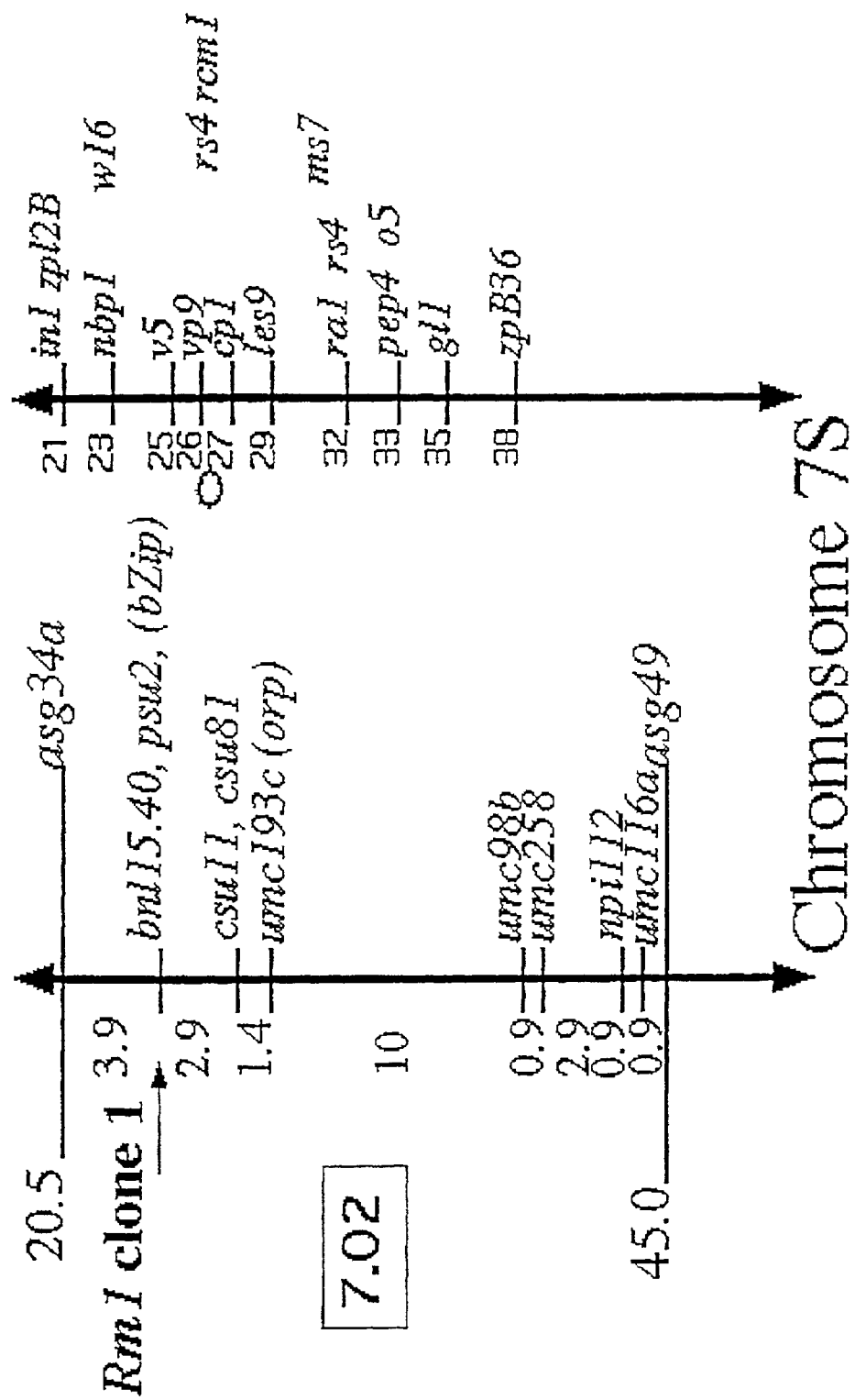
FIG. 3 shows the relative location of the rm1 gene on the short arm of maize chromosome 7.

Primers designed to amplify a unique region of the Rm1 gene were used to amplify this region from maize, oat, and oat-maize monosomic addition lines. A PCR-amplified product was observed only in oat-maize addition line #7. This result was confirmed by Southern blot analysis of the PCR product, thus indicating that the native genomic location of Rm1 in maize is on chromosome 7. A gene-specific DNA probe (the 0.7 kb BamHI-SacII fragment) was used for further mapping and found to map in the vicinity of bn1 15.40 and psu2 (bZip) RFLP markers on the short arm of chromosome 7 (diagrammed in FIG. 3).

D. Isolation of New Insertional Alleles and Confirmation of the Cloning of rm1

A single mutant allele of rm1 had been cloned. Additional mutant alleles were needed to confirm that the rm1 gene had been cloned. To this end, a reverse genetics approach, known by the acronym TUSC (Bensen et al., (1995) *Plant Cell* 7:75–84) was used. TUSC was performed with a gene-specific primer in combination with a Mu-TIR primer. PCR products were amplified from four new insertional alleles of rm1. These PCR products were cloned into the PCR 2.1 TOPO vector (Invitrogen) and then sequenced to identify the exact location of the Mu insertion. While two of these insertions are located 44 bp and 39 bp upstream of the start codon and the TATA box, respectively, two other insertions are at two separate locations within intron 1 (FIG. 2).

F2 seed from all of these events was planted to ascertain whether plants homozygous for these insertional alleles exhibit a rm1 phenotype. Employing a combination of Southern blotting and PCR (using the same set of primers that was used to identify these alleles in the TUSC material), plants homozygous for these new alleles were identified and their phenotype examined. The fact that all plants homozygous for the allele having an insertion 44 bp upstream of the coding region had the rm1 phenotype confirmed the cloning of the rm1 gene. However, plants homozygous with either of the intronic insertions lacked the rm1 phenotype. This is not surprising because such intronic insertions are spliced out along with introns during processing of the transcript into mRNA. The fourth allele, which had insertion 39 bp upstream of the TATA box in the promoter region, failed to transmit to F2. This result is not atypical as TUSC analysis may also pick up Mu insertions that occur in somatic tissues alone.

EXAMPLE 2
Transformation and Regeneration of Transgenic Plants

Immature maize embryos from greenhouse donor plants are bombarded with a plasmid containing the defense-related nucleic acid sequence of the present invention operably linked to a ubiquitin promoter and the selectable marker gene PAT (Wohlleben et al. (1988) *Gene* 70:25–37), which confers resistance to the herbicide Bialaphos. Alternatively, the selectable marker gene is provided on a separate plasmid. Transformation is performed as follows. Media recipes follow below.

A. Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

B. Preparation of DNA

A plasmid vector comprising a defense-related sequence of the invention operably linked to a ubiquitin promoter plus plasmid DNA containing a PAT selectable marker is precipitated onto 1.1 μm (average diameter) tungsten pellets using a $CaCl_2$ precipitation procedure as follows:

100 μl prepared tungsten particles in water
10 μl (1 μg) DNA in Tris EDTA buffer (1 μg total DNA)
100 μl 2.5 M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

C. Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

D. Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for defense-related activity.

E. Bombardment and Culture Media

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos(both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

EXAMPLE 3
Aerobacterium-mediated Transformation Prophetic Example

For Agrobacterium-mediated transformation of maize with a defense-related nucleic acid sequence of the invention preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of Agrobacterium, where the bacteria are capable of transferring the sequence to at least one cell of at least one of the immature embryos (step 1: the infection step). In this step the immature embryos are preferably immersed in an Agrobacterium suspension for the initiation of inoculation. The embryos are co-cultured for a time with the Agrobacterium (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of Agrobacterium without the addition of a selective agent for plant transformants (step 3: resting step). Preferably the immature embryos are cultured on solid medium with antibiotic, but without a selecting agent, for elimination of Agrobacterium and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

EXAMPLE 4
Soybean Embryo Transformation Prophetic Example

Soybean embryos are bombarded with a plasmid containing a defense-related sequence of the invention operably linked to a promoter as follows. To induce somatic embryos, cotyledons, 3–5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327:70–73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188), and the 3' region of the nopaline synthase gene from the T-DNA of the Ti plasmid of *Agrobacterium tumefaciens*. The expression cassette comprising a defense-related sequence of the invention operably linked to the ubiquitin promoter can be isolated as a restriction fragment. This fragment can then be inserted into a unique restriction site of the vector carrying the marker gene.

To 50 μl of a 60 mg/ml 1 μm gold particle suspension is added (in order): 5 μl DNA (1 μg/μl), 20 μl spermidine (0.1 M), and 50 μl $CaCl_2$ (2.5 M). The particle preparation is then agitated for three minutes, spun in a microfuge for 10 seconds and the supernatant removed. The DNA-coated particles are then washed once in 400 μl 70% ethanol and resuspended in 40 μl of anhydrous ethanol. The DNA/particle suspension can be sonicated three times for one second each. Five microliters of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

EXAMPLE 5
Sunflower Meristem Tissue Transformation Prophetic Example

Sunflower meristem tissues are transformed with an expression cassette containing the defense-related nucleotide sequence operably linked to a ubiquitin promoter as follows (see also European Patent Number EP 0 486233, herein incorporated by reference, and Malone-Schoneberg et al. (1994) *Plant Science* 103:199–207). Mature sunflower seed (*Helianthus annuus* L.) are dehulled using a single wheat-head thresher. Seeds are surface sterilized for 30 minutes in a 20% Clorox bleach solution with the addition of two drops of Tween 20 per 50 ml of solution. The seeds are rinsed twice with sterile distilled water.

Split embryonic axis explants are prepared by a modification of procedures described by Schrammeijer et al. (Schrammeijer et al. (1990) *Plant Cell Rep.* 9: 55–60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant.*, 15: 473–497), Shepard's vitamin additions (Shepard (1980) in *Emergent Techniques for the Genetic Improvement of Crops*

(University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid (GA₃), pH 5.6, and 8 g/l Phytagar.

The explants are subjected to microprojectile bombardment prior to Agrobacterium treatment (Bidney et al. (1992) *Plant Mol. Biol.* 18: 301–313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the defense-related gene operably linked to the ubiquitin promoter is introduced into Agrobacterium strain EHAL105 via freeze-thawing as described by Holsters et al. (1978) *Mol. Gen. Genet.* 163:181–187. This plasmid further comprises a kanamycin selectable marker gene (i.e., nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The Agrobacterium cells are pelleted and resuspended at a final $OD_{600}$ of 0.5 in an inoculation medium comprised of 12.5 mM MES pH 5.7, 1 gm/l NH4Cl, and 0.3 gm/l MgSO₄.

Freshly bombarded explants are placed in an Agrobacterium suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for defense-related activity.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by defense-related activity analysis of leaf extracts while transgenic seeds harvested from NPTII-positive $T_0$ plants are identified by defense-related activity analysis of small portions of dry seed cotyledon.

All publications and patent applications mentioned in the specification are indicative of the level of those skilled in the art to which this invention pertains. All publications, patents, and patent applications are hereby incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleic acid molecule having a nucleotide sequence selected from the group consisting of:
   a) a polynucleotide comprising the sequence set forth in SEQ ID NOs: 1 or 2;
   b) a polynucleotide that encodes a polypeptide comprising the amino acid sequence set forth in SEQ ID NO: 3;
   c) a polynucleotide having at least 95% sequence identity to SEQ ID NOs: 1 or 2, wherein said polynucleotide encodes a polypeptide, wherein the expression of said polypeptide in a plant results in necrotic lesions on said plant; and
   d) a polynucleotide comprising a sequence that is the full length complement of the sequence of a), b), or c).

2. A vector comprising the nucleic acid of claim 1.

3. A recombinant expression cassette, comprising the isolated nucleic acid molecule of claim 1 operably linked to a promoter that drives expression in a host cell.

4. A host cell having stably incorporated into its genome at least one nucleotide sequence, wherein said nucleotide sequence Is operably linked to a heterologous promoter that drives expression in the host cell, wherein said nucleotide sequence is selected from the group consisting of:
   a) a polynucleotide comprising the sequence set forth in SEQ ID NOs: 1 or 2;
   b) a polynucleotide that encodes a polypeptide comprising the amino acid sequence set forth in SEQ ID NO: 3;
   c) a polynucleotide having at least 95% sequence identity to SEQ ID NOs: 1 or 2, wherein said polynucleotide encodes a polypeptide, wherein the expression of said polypeptide in a plant results in necrotic lesions on said plant; and
   d) a polynucleotide comprising a sequence that is the full length complement of the sequence of a), b), or c).

5. The host cell of claim 4, wherein said cell is a plant cell.

6. A plant having stably incorporated into its genome at least one polynucleotide, said polynucleotide operably linked to a heterologous promoter that drives expression in a plant cell, wherein said polynucleotide is selected from the group consisting of:
   a) a polynucleotide comprising the sequence set forth in SEQ ID NOs: 1 or 2;
   b) a polynucleotide that encodes a polypeptide comprising the amino acid sequence set forth in SEQ ID NO: 3;
   c) a polynucleotide having at least 95% sequence identity to SEQ ID NOs: 1 or 2, wherein said polynucleotide encodes a polypeptide, wherein the expression of said polypeptide in a plant results in necrotic lesions on said plant; and
   d) a polynucleotide comprising a sequence that is the full length complement of the sequence of a), b), or c).

7. The plant of claim 6, wherein said promoter is a constitutive promoter.

8. The plant of claim 6, wherein said promoter is a tissue-preferred promoter.

9. The plant of claim 6, wherein said promoter is an inducible promoter.

10. The plant of claim 9, wherein said promoter is a pathogen-inducible promoter.

11. The plant of claim 6, wherein said plant is a monocot.

12. The plant of claim 11, wherein said monocot is maize, wheat, rice, barley, sorghum, or rye.

13. The plant of claim 6, wherein said plant is a dicot.

14. A transformed seed of the plant of claim 8.

* * * * *

UNITED STATES PATENT AND TRADEMARK OFFICE
CERTIFICATE OF CORRECTION

PATENT NO. : 6,784,341 B2
DATED : August 31, 2004
INVENTOR(S) : Gurmukh S. Johal and Dilbag Multani It is certified that error appears in the above-identified patent and that said Letters Patent is hereby corrected as shown below:

Column 74,
Line 5, should read:

14. A transformed seed of the plant of claim 6.

Signed and Sealed this

Seventh Day of December, 2004

JON W. DUDAS
*Director of the United States Patent and Trademark Office*

SEQUENCE LISTING

```
<160> NUMBER OF SEQ ID NOS: 9

<210> SEQ ID NO 1
<211> LENGTH: 3120
<212> TYPE: DNA
<213> ORGANISM: Zea mays
<220> FEATURE:
<221> NAME/KEY: misc_feature
<222> LOCATION: (0)...(0)
<223> OTHER INFORMATION: Rm1 genomic sequence

<400> SEQUENCE: 1
ccaataactc agggttaagc aaagcagaac aagaaagcac ctcagctgtc gtagcgctcc      60
tcaccaatcc aatgccgtct ttgacctagc cggcgccgcg tccttgaccg aggaagtagt     120
cgcacgcagc acgctcctat gagctagtaa taattttcac aaccagaatc gcgtgtcgac     180
agcgcgagcc gtaacggaaa ccggatggaa atgggatcca gccggacgcg gggagtctgc     240
tgtcagggcg cacgccatcg agcgaccgtg tcctcgctct tttacctttc ctcctgtcag     300
ggcgcgtgca tcccctacga ccagggcagc gtatatcctt gtcgctcttc gtcgtctccc     360
```

-continued

```
cccacaactg ttatattccc accggcgccg ccggctcttc gtcgtcctcc tccgggtgtg    420
ccccagttcg ctgcccgttc cccagccgcc gatccctcga tctccgctag cttcgttcct    480
tcgtacaggt gcttcacttc atccttgtgc tttctatctg ttcttctcat attgcgtgag    540
aattttcatt tcagttcatg tgagtcgatc cttcaatttt aaaactatgt atgtatgtcg    600
ggtgaacccg gttcctcgat tccccacagg aacggtcagg ggcggaccca gcacccaggc    660
acctcaggcg gtggcctagg ctgcctcgca ggttctgatt gatagaagca agtataatat    720
gtagaaacaa gcaagcaacg tagtatgtac acagcaaaag tataagcaca aaggatcaca    780
gtgtaatctc gcctaggctg tctctaaatc ctgggtccgc cactgggaac ggttgtgttt    840
cagttcatgg gagttggtcc ttcattttta aaaattatgt atgtatgccg ggtgaaatga    900
atccggttcc tcaattcacc acaggaacgg tcgagcagaa actagcagcc actcccgagt    960
cccgactccc gatcgcgatt acttgccgcg gcaccagtac tccagcggcc accatgagca   1020
gcgggaagcg atccttcttc gcgcccaaga agaaggccac caacccgttc gattccgact   1080
ccgacgacga caaaccgcag cagcggccag cgcgggcgtc ctccgtgcct cccccggacg   1140
agcagcgggg ctcctcctct ctcttcggcg ccggcgacag aggcgggctc ttctcttccg   1200
cggccaacca tcactaccgg aacgacttcc gcgacgctgg cggccttgag ggccagtccg   1260
tgcaggagct ggagggctac gcggcgtaca aggccgagga gaccacgcgc cggacgcggg   1320
ggtgcgtcag gatcgccgag gagatgaggg acaccgcatc caagacgctc gtcaccgtcc   1380
accagcaggg gcagcagatc caccgcacgc acatgatggc cgtcgacatc gaccaggatc   1440
tctccagggt aactatagcc ttttcgaatt tctttcgttt gcggtgtggc atcagtttat   1500
gagattgttt gtaccgctag cttagttctg ttcgcctgaa gagggatag tcactgttct   1560 ttcaaatcta gtccgtttca gaaaccctga aacccaacaa gaggaggtgc taactgacta   1620
atttacagag ggtaaattaa acctgcaatc gccaacattt ttgcaagttt atgctgctcc   1680
atttgcacaa gccacaaggc taaccccggg atataaaaga tcttatgcta ataacgagcc   1740
ttattctgct caagtagggc ataatcgcac agcactctca atttcaaacc agaattggac   1800
agttcctgaa atcctgaaat cagcaggtat tctcgctaat aactctagaa attctagttt   1860
tagtggggag ggattaaaac ctggaagtat taacaatgac atgcttgtta gttgttacta   1920
tcggcttttg taactgcata ttgcgactat ggatgctcct ttgcacattg cagacatgtg   1980
acaggtgttg aataaatgtt ttggctcaat atttcagagt gagaagctat tgggcgatct   2040
tgggggtcta ttttccaaaa agtggaagcc aaagaagaat ggcgccatca ggggtcctat   2100
gctaactaga ggtaattact taaactggac tgcatgatga agttgatgac tgaagaaact   2160
tgtactgcct ggtattggct atggtgccgt ccatgactga aaggatgcaa tggtggatgc   2220
agatgattcc ttcataagga aggggagtca tttggagcaa aggcagaaac tagggctggc   2280
agatcatcca cctccatcaa atgcgcgcca attccgttct gaaccctcat cagcacttga   2340
gaaagttgag gtactgtaga cacttgtgaa gctaatgcat ctccagcacg tgatgaaaaa   2400
tcttgatgcg tcttgatatc ctgcatcttt attccataac catctggtcg tttctttgt   2460 agatagagaa ggcaaagcag gatgatgatc tgtctgatct aagcaacata ctgacggagc   2520
tgaaagggat ggccgttgac atgggctctg agatcgagag gtactgttac atttcgctat   2580
cttgtagact gatctgtgtg gtcagtaatt catttatttt cttcctgttg tatagtcaat   2640
tctcaagaaa gtatccgaaa cttccaaaaa gaaaatacta tctgtcagtt tgaatgctga   2700
```

-continued

```
tagcaatctc gttagttatt aaattattaa tttggagtat tgttgctgtg agtatgacat    2760
gtcctctgtg tttgttggat tcaggcaaac aaaagcaatg ggggatgcag agaaggatta    2820 tgacagctg aacttcaggg tcaagggagc aaacactcga gctcgccgtc tcctcgggag     2880
ataaaaaaat gcatatattc ttgtctcttg gatggtccat aacacattaa ctatatgggg    2940
gcatcaaatt ctgatgattt tgtgcatcag attttgatta gcattgttac cgtggacatg    3000
tcggcgtgta tggtagttga gacatatttt atatgtttgc ttcttttttc tattttttta    3060
gcattgcacg agcttaggat ttcagtggat tttacatgga aaaccttgtc tgattagaaa    3120
```

<210> SEQ ID NO 2
<211> LENGTH: 1265
<212> TYPE: DNA
<213> ORGANISM: Zea mays
<220> FEATURE:
<221> NAME/KEY: misc_feature
<222> LOCATION: (0)...(0)
<223> OTHER INFORMATION: SNAP25 cDNA
<221> NAME/KEY: CDS
<222> LOCATION: (157)...(1008)

<400> SEQUENCE: 2

```
cccagttcgc tgcccgttcc ccagccgccg atccctcgat ctccgctagc ttcgttcctt     60
cgtacaggaa cggtcgagca gaaactagca gccactcccg agtcccgact cccgatcgcg    120
attacttgcc gcggcaccag tactccagcg ccacc atg agc agc ggg aag cga        174
                                       Met Ser Ser Gly Lys Arg
                                         1               5 tcc ttc ttc gcg ccc aag aag aag gcc acc aac ccg ttc gat tcc gac      222
Ser Phe Phe Ala Pro Lys Lys Lys Ala Thr Asn Pro Phe Asp Ser Asp
              10                  15                  20 tcc gac gac gac aaa ccg cag cag cgg cca gcg cgg gcg tcc tcc gtg      270
Ser Asp Asp Asp Lys Pro Gln Gln Arg Pro Ala Arg Ala Ser Ser Val
     25                  30                  35 cct ccc ccg gac gag cag cgg ggc tcc tcc tct ctc ttc ggc gcc ggc      318
Pro Pro Pro Asp Glu Gln Arg Gly Ser Ser Ser Leu Phe Gly Ala Gly
 40                  45                  50 gac aga ggc ggg ctc ttc tct tcc gcg gcc aac cat cac tac cgg aac      366
Asp Arg Gly Gly Leu Phe Ser Ser Ala Ala Asn His His Tyr Arg Asn
 55                  60                  65                  70 gac ttc cgc gac gct ggc ggc ctt gag ggc cag tcc gtg cag gag ctg      414
Asp Phe Arg Asp Ala Gly Gly Leu Glu Gly Gln Ser Val Gln Glu Leu
             75                  80                  85 gag ggc tac gcg gcg tac aag gcc gag gag acc acg cgc cgg acg cgg      462
Glu Gly Tyr Ala Ala Tyr Lys Ala Glu Glu Thr Thr Arg Arg Thr Arg
         90                  95                 100 ggg tgc gtc agg atc gcc gag gag atg agg gac acc gca tcc aag acg      510
Gly Cys Val Arg Ile Ala Glu Glu Met Arg Asp Thr Ala Ser Lys Thr
     105                 110                 115 ctc gtc acc gtc cac cag cag ggg cag cag atc cac cgc acg cac atg      558
Leu Val Thr Val His Gln Gln Gly Gln Gln Ile His Arg Thr His Met
 120                 125                 130 atg gcc gtc gac atc gac cag gat ctc tcc agg agt gag aag cta ttg      606
Met Ala Val Asp Ile Asp Gln Asp Leu Ser Arg Ser Glu Lys Leu Leu
135                 140                 145                 150 ggc gat ctt ggg ggt cta ttt tcc aaa aag tgg aag cca aag aag aat      654
Gly Asp Leu Gly Gly Leu Phe Ser Lys Lys Trp Lys Pro Lys Lys Asn
             155                 160                 165 ggc gcc atc agg ggt cct atg cta act aga gat gat tcc ttc ata agg      702
Gly Ala Ile Arg Gly Pro Met Leu Thr Arg Asp Asp Ser Phe Ile Arg
         170                 175                 180
```

-continued

```
aag ggg agt cat ttg gag caa agg cag aaa cta ggg ctg gca gat cat      750
Lys Gly Ser His Leu Glu Gln Arg Gln Lys Leu Gly Leu Ala Asp His
            185                 190                 195 cca cct cca tca aat gcg cgc caa ttc cgt tct gaa ccc tca tca gca      798
Pro Pro Pro Ser Asn Ala Arg Gln Phe Arg Ser Glu Pro Ser Ser Ala
200                 205                 210 ctt gag aaa gtt gag ata gag aag gca aag cag gat gat gat ctg tct      846
Leu Glu Lys Val Glu Ile Glu Lys Ala Lys Gln Asp Asp Asp Leu Ser
215                 220                 225                 230 gat cta agc aac ata ctg acg gag ctg aaa ggg atg gcc gtt gac atg      894
Asp Leu Ser Asn Ile Leu Thr Glu Leu Lys Gly Met Ala Val Asp Met
            235                 240                 245 ggc tct gag atc gag agg caa aca aaa gca atg ggg gat gca gag aag      942
Gly Ser Glu Ile Glu Arg Gln Thr Lys Ala Met Gly Asp Ala Glu Lys
        250                 255                 260 gat tat gac gag ctg aac ttc agg gtc aag gga gca aac act cga gct      990
Asp Tyr Asp Glu Leu Asn Phe Arg Val Lys Gly Ala Asn Thr Arg Ala
265                 270                 275 cgc cgt ctc ctc ggg aga taaaaaaatg catatattct tgtctcttgg            1038
Arg Arg Leu Leu Gly Arg
    280 atggtccata acacattaac tatatggggg catcaaattc tgatgatttt gtgcatcaga    1098 ttttgattag cattgttacc gtggacatgt cggcgtgtat ggtagttgag acatatttta    1158 tatgtttgct tctttttcct atttttttag cattgcacga gcttaggatt tcagtggatt    1218 ttacatggaa aaccttgtct gattagaaaa aaaaaaaaaa aaaaaa                   1265

<210> SEQ ID NO 3
<211> LENGTH: 284
<212> TYPE: PRT
<213> ORGANISM: Zea mays

<400> SEQUENCE: 3

Met Ser Ser Gly Lys Arg Ser Phe Phe Ala Pro Lys Lys Lys Ala Thr
1               5                   10                  15

Asn Pro Phe Asp Ser Asp Ser Asp Asp Lys Pro Gln Gln Arg Pro
            20                  25                  30

Ala Arg Ala Ser Ser Val Pro Pro Asp Glu Gln Arg Gly Ser Ser
        35                  40                  45

Ser Leu Phe Gly Ala Gly Asp Arg Gly Gly Leu Phe Ser Ser Ala Ala
    50                  55                  60

Asn His His Tyr Arg Asn Asp Phe Arg Asp Ala Gly Gly Leu Glu Gly
65                  70                  75                  80

Gln Ser Val Gln Glu Leu Glu Gly Tyr Ala Ala Tyr Lys Ala Glu Glu
                85                  90                  95

Thr Thr Arg Arg Thr Arg Gly Cys Val Arg Ile Ala Glu Glu Met Arg
            100                 105                 110

Asp Thr Ala Ser Lys Thr Leu Val Thr Val His Gln Gly Gln Gln
        115                 120                 125

Ile His Arg Thr His Met Met Ala Val Asp Ile Asp Gln Asp Leu Ser
    130                 135                 140

Arg Ser Glu Lys Leu Leu Gly Asp Leu Gly Gly Leu Phe Ser Lys Lys
145                 150                 155                 160

Trp Lys Pro Lys Lys Asn Gly Ala Ile Arg Gly Pro Met Leu Thr Arg
                165                 170                 175

Asp Asp Ser Phe Ile Arg Lys Gly Ser His Leu Glu Gln Arg Gln Lys
```

```
                        180             185                 190
Leu Gly Leu Ala Asp His Pro Pro Ser Asn Ala Arg Gln Phe Arg
        195                 200                 205

Ser Glu Pro Ser Ser Ala Leu Glu Lys Val Glu Ile Glu Lys Ala Lys
        210                 215                 220

Gln Asp Asp Leu Ser Asp Leu Ser Asn Ile Leu Thr Glu Leu Lys
225                 230                 235                 240

Gly Met Ala Val Asp Met Gly Ser Glu Ile Glu Arg Gln Thr Lys Ala
                245                 250                 255

Met Gly Asp Ala Glu Lys Asp Tyr Asp Glu Leu Asn Phe Arg Val Lys
                260                 265                 270

Gly Ala Asn Thr Arg Ala Arg Arg Leu Leu Gly Arg
                275                 280

<210> SEQ ID NO 4
<211> LENGTH: 1178
<212> TYPE: DNA
<213> ORGANISM: Oryza sativa
<220> FEATURE:
<221> NAME/KEY: misc_feature
<222> LOCATION: (0)...(0)
<223> OTHER INFORMATION: SNAP25 cDNA
<221> NAME/KEY: CDS
<222> LOCATION: (83)...(931)

<400> SEQUENCE: 4
```

| | | |
|---|---|---:|
| gaattcggca cgagggcata ttcagtttca tttgtgcgca gaaacttgct tgctgcggaa | | 60 |
| tctgacccaa ggagttttcg ag atg agc ggg agg aga tcg ttc ttc gca tcc | | 112 |
|                               Met Ser Gly Arg Arg Ser Phe Phe Ala Ser | | |
|                            1          5            10 | | |

```
aag aag ccg tcg cgg agc agc aac ccc ttc gac tcc gac tcc gac gat    160
Lys Lys Pro Ser Arg Ser Ser Asn Pro Phe Asp Ser Asp Ser Asp Asp
            15                  20                  25 ggc ggg agg gag cag aga ccg gcg agg gcc tcc tcc gtg cct cct ccg    208
Gly Gly Arg Glu Gln Arg Pro Ala Arg Ala Ser Ser Val Pro Pro Pro
        30                  35                  40 gcc gac cag cgg ggc tcc ctc ttc ggc ggc ggg gat ggc ttc tcc gcc    256
Ala Asp Gln Arg Gly Ser Leu Phe Gly Gly Gly Asp Gly Phe Ser Ala
    45                  50                  55 tcg tcg gcg gcg gcg agg agc cgg tac agg aac gac ttc cgc gac acc    304
Ser Ser Ala Ala Ala Arg Ser Arg Tyr Arg Asn Asp Phe Arg Asp Thr
60                  65                  70 ggc ggc gtg gag gcc caa tcg gtg caa gag ctg gag ggc tac gcg gcg    352
Gly Gly Val Glu Ala Gln Ser Val Gln Glu Leu Glu Gly Tyr Ala Ala
75                  80                  85                  90 tac aag gcg gag gag acc act cag cgg gtg cag ggc tgc gtc cgc atc    400
Tyr Lys Ala Glu Glu Thr Thr Gln Arg Val Gln Gly Cys Val Arg Ile
                95                  100                 105 gcc gag gag atg agg gat acc gcg tcc aag aac ctc gtc acc ata cac    448
Ala Glu Glu Met Arg Asp Thr Ala Ser Lys Asn Leu Val Thr Ile His
            110                 115                 120 caa caa ggg cag cag atc acc cgc acg cac atg atg acc ctc gac atc    496
Gln Gln Gly Gln Gln Ile Thr Arg Thr His Met Met Thr Leu Asp Ile
        125                 130                 135 gac caa gat ttc tcc agg agc gag aag ctg ctg ggt gat ctt ggg ggt    544
Asp Gln Asp Phe Ser Arg Ser Glu Lys Leu Leu Gly Asp Leu Gly Gly
    140                 145                 150 ata ttt tcc aaa aag tgg aag cca aaa aag aat gga gaa ata tcg ggg    592
Ile Phe Ser Lys Lys Trp Lys Pro Lys Lys Asn Gly Glu Ile Ser Gly
155                 160                 165                 170
```

-continued

```
cct atg cta act aga gat gat tcc ttc att cgg aag ggc agc cat ttg    640
Pro Met Leu Thr Arg Asp Asp Ser Phe Ile Arg Lys Gly Ser His Leu
            175                 180                 185 gaa caa agg cac aaa ctg gga cta tcg gat cac cca cct caa tcg aat    688
Glu Gln Arg His Lys Leu Gly Leu Ser Asp His Pro Pro Gln Ser Asn
        190                 195                 200 gca cgc caa ttc cat tcc gag cca act tca gcc ttc cag aaa gtg gag    736
Ala Arg Gln Phe His Ser Glu Pro Thr Ser Ala Phe Gln Lys Val Glu
    205                 210                 215 atg gag aag gca aag cag gat gtt ggc cta tct aat cta agt aac ata    784
Met Glu Lys Ala Lys Gln Asp Val Gly Leu Ser Asn Leu Ser Asn Ile
220                 225                 230 ttg acc gag ctg aaa ggc atg gcg gtt gac atg ggc act gag att gac    832
Leu Thr Glu Leu Lys Gly Met Ala Val Asp Met Gly Thr Glu Ile Asp
235                 240                 245                 250 aga caa aca aag gct ttg gga gat tca gag aag gac tac gac gaa ttg    880
Arg Gln Thr Lys Ala Leu Gly Asp Ser Glu Lys Asp Tyr Asp Glu Leu
            255                 260                 265 aac ttc agg atc aag gga gca aac act cgg gca cgc cgt ttg ctt gga    928
Asn Phe Arg Ile Lys Gly Ala Asn Thr Arg Ala Arg Arg Leu Leu Gly
        270                 275                 280 aaa taaactgcag aatataatct catcacagga caggagtcct tccatccctt         981
Lys ttacccttag tcttgtggag gataattaat tgttttgtgg gccattggtt ctgatgattc  1041
tgtgcatcag attttgatca gtacggtgaa tggttggtcc tggatatgtc agggtataat  1101
gtatctgtat atactgctat agccattagc cagtaaaaaa aaaaaaaaaa aaaaaaaaaa  1161
aaaaaaaaaa aaaaaaa                                                1178
```

<210> SEQ ID NO 5
<211> LENGTH: 283
<212> TYPE: PRT
<213> ORGANISM: Oryza sativa

<400> SEQUENCE: 5

Met Ser Gly Arg Arg Ser Phe Phe Ala Ser Lys Lys Pro Ser Arg Ser
1               5                   10                  15

Ser Asn Pro Phe Asp Ser Asp Ser Asp Asp Gly Gly Arg Glu Gln Arg
            20                  25                  30

Pro Ala Arg Ala Ser Ser Val Pro Pro Ala Asp Gln Arg Gly Ser
        35                  40                  45

Leu Phe Gly Gly Gly Asp Gly Phe Ser Ala Ser Ser Ala Ala Ala Arg
    50                  55                  60

Ser Arg Tyr Arg Asn Asp Phe Arg Asp Thr Gly Gly Val Glu Ala Gln
65                  70                  75                  80

Ser Val Gln Glu Leu Glu Gly Tyr Ala Ala Tyr Lys Ala Glu Glu Thr
                85                  90                  95

Thr Gln Arg Val Gln Gly Cys Val Arg Ile Ala Glu Glu Met Arg Asp
            100                 105                 110

Thr Ala Ser Lys Asn Leu Val Thr Ile His Gln Gln Gly Gln Gln Ile
        115                 120                 125

Thr Arg Thr His Met Met Thr Leu Asp Ile Asp Gln Asp Phe Ser Arg
    130                 135                 140

Ser Glu Lys Leu Leu Gly Asp Leu Gly Gly Ile Phe Ser Lys Lys Trp
145                 150                 155                 160

Lys Pro Lys Lys Asn Gly Glu Ile Ser Gly Pro Met Leu Thr Arg Asp

-continued

```
                          165                 170                 175
Asp Ser Phe Ile Arg Lys Gly Ser His Leu Glu Gln Arg His Lys Leu
            180                 185                 190

Gly Leu Ser Asp His Pro Pro Gln Ser Asn Ala Arg Gln Phe His Ser
        195                 200                 205

Glu Pro Thr Ser Ala Phe Gln Lys Val Glu Met Glu Lys Ala Lys Gln
    210                 215                 220

Asp Val Gly Leu Ser Asn Leu Ser Asn Ile Leu Thr Glu Leu Lys Gly
225                 230                 235                 240

Met Ala Val Asp Met Gly Thr Glu Ile Asp Arg Gln Thr Lys Ala Leu
                245                 250                 255

Gly Asp Ser Glu Lys Asp Tyr Asp Glu Leu Asn Phe Arg Ile Lys Gly
            260                 265                 270

Ala Asn Thr Arg Ala Arg Arg Leu Leu Gly Lys
        275                 280

<210> SEQ ID NO 6
<211> LENGTH: 1178
<212> TYPE: DNA
<213> ORGANISM: Triticum aestivum
<220> FEATURE:
<221> NAME/KEY: misc_feature
<222> LOCATION: (1)...(1178)
<223> OTHER INFORMATION: n = A,T,C or G
<221> NAME/KEY: misc_feature
<222> LOCATION: (0)...(0)
<223> OTHER INFORMATION: SNAP25 cDNA
<221> NAME/KEY: CDS
<222> LOCATION: (61)...(969)
<221> NAME/KEY: misc_feature
<222> LOCATION: 1158
<223> OTHER INFORMATION: n = A,T,C or G

<400> SEQUENCE: 6
attaccagca gcagagcaga gatctcggcc tgctgctcgg cgccaggggc tccttctgcc       60 atg agc gcc gcc agg tcc tcc ttc ttc gcc tcc aac aac gcc aag aag      108
Met Ser Ala Ala Arg Ser Ser Phe Phe Ala Ser Asn Asn Ala Lys Lys
  1               5                  10                  15 aag ccc gcc gcc gcc cgg aac ccc ttc gac tcc gac tcg gac gac gac      156
Lys Pro Ala Ala Ala Arg Asn Pro Phe Asp Ser Asp Ser Asp Asp Asp
             20                  25                  30 ggc atg gtc cag cgg cgg ggc ccg gcg cgg gcc tcc tcc gtc ccg          204
Gly Met Val Gln Arg Arg Gly Pro Ala Arg Ala Ser Ser Val Pro
         35                  40                  45 acc ccc gcc gcc gcg ccg gcc agg gcc gac gag cgg gac tcc ctc ttc      252
Thr Pro Ala Ala Ala Pro Ala Arg Ala Asp Glu Arg Asp Ser Leu Phe
 50                  55                  60 gcc ggc ggc ggc cca gcg caa tcc ggc ttc gcg tcc tcc tcc tcc tcg      300
Ala Gly Gly Gly Pro Ala Gln Ser Gly Phe Ala Ser Ser Ser Ser Ser
 65                  70                  75                  80 tcc gcg gcg gcc aag ggc cgg tac agg aac gac ttt cgg gac tcc ggg      348
Ser Ala Ala Ala Lys Gly Arg Tyr Arg Asn Asp Phe Arg Asp Ser Gly
                 85                  90                  95 ggc gtg gag gcg cag tcg gtg cag gag ttg gag ggg tac gcg gcc tac      396
Gly Val Glu Ala Gln Ser Val Gln Glu Leu Glu Gly Tyr Ala Ala Tyr
            100                 105                 110 aag gcc gag gag acc acg cgc cgg gtc gac gga tgc ctc cgg gtc gcc      444
Lys Ala Glu Glu Thr Thr Arg Arg Val Asp Gly Cys Leu Arg Val Ala
        115                 120                 125 gag gag atg cgg gac acc gcc tcc aag acc ctg ctc cac gtg cac cag      492
Glu Glu Met Arg Asp Thr Ala Ser Lys Thr Leu Leu His Val His Gln
```

```
cag ggc cag cag atc cgg cgc acc cac gcc atg gcc ctc gac atc gac    540
Gln Gly Gln Gln Ile Arg Arg Thr His Ala Met Ala Leu Asp Ile Asp
145                 150                 155                 160 cag gat ctc tcc agg agt gag aag cta ttg ggc gat ctt ggg ggt cta    588
Gln Asp Leu Ser Arg Ser Glu Lys Leu Leu Gly Asp Leu Gly Gly Leu
                165                 170                 175 ttt tcc aaa aag tgg aag cca aag aag aat ggc gcc atc agg ggt cct    636
Phe Ser Lys Lys Trp Lys Pro Lys Lys Asn Gly Ala Ile Arg Gly Pro
            180                 185                 190 atg cta act aga gat gat tcc ttc ata agg aag ggg agt cat ttg gag    684
Met Leu Thr Arg Asp Asp Ser Phe Ile Arg Lys Gly Ser His Leu Glu
        195                 200                 205 caa agg cag aaa cta ggg ctg gca gtt cat cca cct cca tca aat gcg    732
Gln Arg Gln Lys Leu Gly Leu Ala Val His Pro Pro Pro Ser Asn Ala
    210                 215                 220 cgc caa ttc cca tcc gaa ccc acg tca gag ctt gag aaa gtt gag gtg    780
Arg Gln Phe Pro Ser Glu Pro Thr Ser Glu Leu Glu Lys Val Glu Val
225                 230                 235                 240 gag aaa gga aag cag gat gat gag cta tct gat ctt aac gac ata ctg    828
Glu Lys Gly Lys Gln Asp Asp Glu Leu Ser Asp Leu Asn Asp Ile Leu
                245                 250                 255 acc gag ttg aaa gga atg gcc gtt gac atg gga act gag att cag agg    876
Thr Glu Leu Lys Gly Met Ala Val Asp Met Gly Thr Glu Ile Gln Arg
            260                 265                 270 caa aca aaa gca tgg ggg cat gca gag aag ctt ttt gcc aac ttt gac    924
Gln Thr Lys Ala Trp Gly His Ala Glu Lys Leu Phe Ala Asn Phe Asp
        275                 280                 285 tac agg tcc aag ggg gcg aac acc cac tcg cgt ccg ctt ggg gga        969
Tyr Arg Ser Lys Gly Ala Asn Thr His Ser Arg Pro Leu Gly Gly
    290                 295                 300 taaaaatgaa catccctggc ccttgggtgg cctaatacac attactttgg gggacaaatt 1029 gatgattgtc atcaacattt gatatacact gtaacgatgg cattgcgacg tgtagggatt 1089 ggaatagtta atgttgtcct ttcaatttta atgtcactta gtttcagttt tatgaacctt 1149 cggtactcnt tcgaaaaggg caaaaaaaa                                   1178

<210> SEQ ID NO 7
<211> LENGTH: 303
<212> TYPE: PRT
<213> ORGANISM: Triticum aestivum

<400> SEQUENCE: 7

Met Ser Ala Ala Arg Ser Ser Phe Phe Ala Ser Asn Asn Ala Lys Lys
 1               5                  10                  15

Lys Pro Ala Ala Ala Arg Asn Pro Phe Asp Ser Asp Ser Asp Asp Asp
                20                  25                  30

Gly Gly Met Val Gln Arg Arg Gly Pro Ala Arg Ala Ser Ser Val Pro
            35                  40                  45

Thr Pro Ala Ala Ala Pro Ala Arg Ala Asp Glu Arg Asp Ser Leu Phe
        50                  55                  60

Ala Gly Gly Gly Pro Ala Gln Ser Gly Phe Ala Ser Ser Ser Ser Ser
65                  70                  75                  80

Ser Ala Ala Ala Lys Gly Arg Tyr Arg Asn Asp Phe Arg Asp Ser Gly
                85                  90                  95

Gly Val Glu Ala Gln Ser Val Gln Glu Leu Glu Gly Tyr Ala Ala Tyr
            100                 105                 110
```

-continued

```
Lys Ala Glu Glu Thr Thr Arg Arg Val Asp Gly Cys Leu Arg Val Ala
            115                 120                 125
Glu Glu Met Arg Asp Thr Ala Ser Lys Thr Leu Leu His Val His Gln
        130                 135                 140
Gln Gly Gln Gln Ile Arg Arg Thr His Ala Met Ala Leu Asp Ile Asp
145                 150                 155                 160
Gln Asp Leu Ser Arg Ser Glu Lys Leu Leu Gly Asp Leu Gly Gly Leu
                165                 170                 175
Phe Ser Lys Lys Trp Lys Pro Lys Lys Asn Gly Ala Ile Arg Gly Pro
            180                 185                 190
Met Leu Thr Arg Asp Asp Ser Phe Ile Arg Lys Gly Ser His Leu Glu
        195                 200                 205
Gln Arg Gln Lys Leu Gly Leu Ala Val His Pro Pro Ser Asn Ala
    210                 215                 220
Arg Gln Phe Pro Ser Glu Pro Thr Ser Glu Leu Glu Lys Val Glu Val
225                 230                 235                 240
Glu Lys Gly Lys Gln Asp Asp Glu Leu Ser Asp Leu Asn Asp Ile Leu
                245                 250                 255
Thr Glu Leu Lys Gly Met Ala Val Asp Met Gly Thr Glu Ile Gln Arg
            260                 265                 270
Gln Thr Lys Ala Trp Gly His Ala Glu Lys Leu Phe Ala Asn Phe Asp
        275                 280                 285
Tyr Arg Ser Lys Gly Ala Asn Thr His Ser Arg Pro Leu Gly Gly
    290                 295                 300

<210> SEQ ID NO 8
<211> LENGTH: 1219
<212> TYPE: DNA
<213> ORGANISM: Arabidopsis thaliana
<220> FEATURE:
<221> NAME/KEY: misc_feature
<222> LOCATION: (0)...(0)
<223> OTHER INFORMATION: SNAP25 cDNA
<221> NAME/KEY: CDS
<222> LOCATION: (187)...(1089)

<400> SEQUENCE: 8
cttcttcgca ttgatttggt cctccttcct cttctattct attcattaag aacctaatct      60
tcatcttctc catcttcttc ttcacggact ccacttcgct catccaggaa ggtttattag     120
tagtaaccaa tccaagtgtt cctttttgttt gaagcaacaa gctttgtgat attatccctga    180 gagaca atg ttt ggt tta agg aaa tca ccg gca aat ctt ccc aag cat        228
       Met Phe Gly Leu Arg Lys Ser Pro Ala Asn Leu Pro Lys His
         1               5                  10 aac tca gtc gac ctc aag tct tcc aag cca aat cct ttc gat tca gat       276
Asn Ser Val Asp Leu Lys Ser Ser Lys Pro Asn Pro Phe Asp Ser Asp
 15                  20                  25                  30 gat gaa tct gac aac aaa cat acc ctt aac cct tct aag agg act acc       324
Asp Glu Ser Asp Asn Lys His Thr Leu Asn Pro Ser Lys Arg Thr Thr
                 35                  40                  45 tct gaa ccc tct ttg gct gat atg aca aac cct ttt ggt ggt gag aga       372
Ser Glu Pro Ser Leu Ala Asp Met Thr Asn Pro Phe Gly Gly Glu Arg
             50                  55                  60 gtt cag aaa gga gat agt agt tca tcc aaa cag tca ttg ttt tcg aac       420
Val Gln Lys Gly Asp Ser Ser Ser Ser Lys Gln Ser Leu Phe Ser Asn
         65                  70                  75 tcc aaa tac cag tac aag aac aat ttc cgt gat tct ggt ggt att gaa       468
Ser Lys Tyr Gln Tyr Lys Asn Asn Phe Arg Asp Ser Gly Gly Ile Glu
     80                  85                  90
```

```
aac cag tcg gtt cag gag ctt gaa ggt tat gct gtg tac aag gct gaa       516
Asn Gln Ser Val Gln Glu Leu Glu Gly Tyr Ala Val Tyr Lys Ala Glu
 95                 100                 105                 110 gag act acg aaa tct gta caa ggt tgt ttg aag gta gca gaa gat ata       564
Glu Thr Thr Lys Ser Val Gln Gly Cys Leu Lys Val Ala Glu Asp Ile
                115                 120                 125 agg tct gat gct acc aga act ttg gtc atg tta cac gat cag ggc gag       612
Arg Ser Asp Ala Thr Arg Thr Leu Val Met Leu His Asp Gln Gly Glu
            130                 135                 140 caa atc act agg acg cac cat aaa gcc gtt gaa atc gac cat gat ctc       660
Gln Ile Thr Arg Thr His His Lys Ala Val Glu Ile Asp His Asp Leu
        145                 150                 155 agt cgt ggt gag aaa ctt ctt gga agc ctt gga ggc atg ttt tca aag       708
Ser Arg Gly Glu Lys Leu Leu Gly Ser Leu Gly Gly Met Phe Ser Lys
    160                 165                 170 act tgg aaa cca aag aag act cgt cct ata aat ggt ccc gtc gta acc       756
Thr Trp Lys Pro Lys Lys Thr Arg Pro Ile Asn Gly Pro Val Val Thr
175                 180                 185                 190 aga gat gac tca cca acg aga aga gtt aac cac tta gag aaa agg gaa       804
Arg Asp Asp Ser Pro Thr Arg Arg Val Asn His Leu Glu Lys Arg Glu
                195                 200                 205 aaa ctg gga ctg aac tca gca ccc aga gga caa tca aga acc cga gaa       852
Lys Leu Gly Leu Asn Ser Ala Pro Arg Gly Gln Ser Arg Thr Arg Glu
            210                 215                 220 cca ctc ccc gaa tca gct gat gct tat cag aga gtg gag atg gaa aaa       900
Pro Leu Pro Glu Ser Ala Asp Ala Tyr Gln Arg Val Glu Met Glu Lys
        225                 230                 235 gct aag caa gac gat ggg ctt tca gac ttg agt gat ata ctc ggc gag       948
Ala Lys Gln Asp Asp Gly Leu Ser Asp Leu Ser Asp Ile Leu Gly Glu
    240                 245                 250 cta aag aac atg gct gtt gac atg gga agc gaa atc gag aag cag aac       996
Leu Lys Asn Met Ala Val Asp Met Gly Ser Glu Ile Glu Lys Gln Asn
255                 260                 265                 270 aaa gga ctt gac cat ctt cat gat gat gtt gac gaa ctc aac ttc aga      1044
Lys Gly Leu Asp His Leu His Asp Asp Val Asp Glu Leu Asn Phe Arg
                275                 280                 285 gtg caa caa tca aac caa cgt ggt cgc cgt ttg ctt gga aag tag          1089
Val Gln Gln Ser Asn Gln Arg Gly Arg Arg Leu Leu Gly Lys  *
            290                 295                 300 atgaacagag ggtttatatg ttcattacac tcattcctcg tttgttttat tctctatgaa    1149
gttgttcttt aaaactggaa agattcttat catgttaaat acattattgc tatcaaaaaa    1209
aaaaaaaaaa                                                           1219

<210> SEQ ID NO 9
<211> LENGTH: 300
<212> TYPE: PRT
<213> ORGANISM: Arabidopsis

<400> SEQUENCE: 9

Met Phe Gly Leu Arg Lys Ser Pro Ala Asn Leu Pro Lys His Asn Ser
 1               5                  10                  15

Val Asp Leu Lys Ser Ser Lys Pro Asn Pro Phe Asp Ser Asp Asp Glu
            20                  25                  30

Ser Asp Asn Lys His Thr Leu Asn Pro Ser Lys Arg Thr Thr Ser Glu
        35                  40                  45

Pro Ser Leu Ala Asp Met Thr Asn Pro Phe Gly Gly Glu Arg Val Gln
    50                  55                  60
```

-continued

```
Lys Gly Asp Ser Ser Ser Ser Lys Gln Ser Leu Phe Ser Asn Ser Lys
 65                  70                  75                  80

Tyr Gln Tyr Lys Asn Asn Phe Arg Asp Ser Gly Gly Ile Glu Asn Gln
             85                  90                  95

Ser Val Gln Glu Leu Glu Gly Tyr Ala Val Tyr Lys Ala Glu Glu Thr
            100                 105                 110

Thr Lys Ser Val Gln Gly Cys Leu Lys Val Ala Glu Asp Ile Arg Ser
            115                 120                 125

Asp Ala Thr Arg Thr Leu Val Met Leu His Asp Gln Gly Glu Gln Ile
        130                 135                 140

Thr Arg Thr His His Lys Ala Val Glu Ile Asp His Asp Leu Ser Arg
145                 150                 155                 160

Gly Glu Lys Leu Leu Gly Ser Leu Gly Gly Met Phe Ser Lys Thr Trp
            165                 170                 175

Lys Pro Lys Lys Thr Arg Pro Ile Asn Gly Pro Val Val Thr Arg Asp
            180                 185                 190

Asp Ser Pro Thr Arg Arg Val Asn His Leu Glu Lys Arg Glu Lys Leu
        195                 200                 205

Gly Leu Asn Ser Ala Pro Arg Gly Gln Ser Arg Thr Arg Glu Pro Leu
        210                 215                 220

Pro Glu Ser Ala Asp Ala Tyr Gln Arg Val Glu Met Glu Lys Ala Lys
225                 230                 235                 240

Gln Asp Asp Gly Leu Ser Asp Leu Ser Asp Ile Leu Gly Glu Leu Lys
            245                 250                 255

Asn Met Ala Val Asp Met Gly Ser Glu Ile Glu Lys Gln Asn Lys Gly
            260                 265                 270

Leu Asp His Leu His Asp Asp Val Asp Glu Leu Asn Phe Arg Val Gln
        275                 280                 285

Gln Ser Asn Gln Arg Gly Arg Arg Leu Leu Gly Lys
        290                 295                 300
```